(12) United States Patent
Tannhauser et al.

(10) Patent No.: US 11,723,653 B2
(45) Date of Patent: Aug. 15, 2023

(54) COMPOSITE SUTURE NEEDLES HAVING ELASTICALLY DEFORMABLE SECTIONS

(71) Applicant: Ethicon, Inc., Somerville, NJ (US)

(72) Inventors: Robert J. Tannhauser, Bridgewater, NJ (US); Frank Richard Cichocki, Jr., Easton, NJ (US)

(73) Assignee: Ethicon, Inc., Raritan, NJ (US)

( * ) Notice: Subject to any disclaimer, the term of this patent is extended or adjusted under 35 U.S.C. 154(b) by 0 days.

(21) Appl. No.: 16/845,354

(22) Filed: Apr. 10, 2020

(65) Prior Publication Data

US 2021/0315569 A1   Oct. 14, 2021

(51) Int. Cl.
  *A61B 17/06*  (2006.01)
  *A61B 17/04*  (2006.01)
  *A61B 17/00*  (2006.01)

(52) U.S. Cl.
  CPC .... *A61B 17/06066* (2013.01); *A61B 17/0469* (2013.01); *A61B 2017/00867* (2013.01); *A61B 2017/0608* (2013.01); *A61B 2017/06095* (2013.01)

(58) Field of Classification Search
  CPC .......... A61B 17/06066; A61B 17/0469; A61B 2017/0608; A61B 2017/06095; A61B 2017/00867; A61B 2017/0609; A61B 2017/0618; A61B 2017/0645; A61B 17/06004; A61B 17/06114; A61B 17/062;
  (Continued)

(56) References Cited

U.S. PATENT DOCUMENTS 3,799,169 A * 3/1974 Beroff .............. A61B 17/06004
                                              606/224
5,358,498 A * 10/1994 Shave .............. A61B 17/06004
                                              606/224
6,159,233 A    12/2000 Matsuzawa
                (Continued)

FOREIGN PATENT DOCUMENTS

CN      106456141         2/2017
CN      108578221 A       9/2018
                (Continued)

OTHER PUBLICATIONS

International Search Report of the International Searching Authority issued in corresponding International Application No. PCT/IB2021/052501, dated Aug. 17, 2021, 8 pages.
(Continued)

*Primary Examiner* — Kathleen S Holwerda
*Assistant Examiner* — Lauren Dubose

(57) ABSTRACT

A composite suture needle configured for passing through a smaller cannula used in minimally invasive surgery includes a curved elongated body made of stainless steel. The curved elongated body has a proximal end and a distal end with a pointed tip. The composite suture needle includes a sheath overlying the curved elongated body. The sheath is curved for conforming to the shape of the curved elongated body. The sheath is made of a material that is more elastic than the curved elongated body. The pointed tip of the curved elongated body extends distally beyond the distal end of the sheath. The curved elongated body is made of stainless steel and the sheath is made of a material, such as nitinol, that is more elastic than the elongated body.

20 Claims, 23 Drawing Sheets

(58) Field of Classification Search
CPC ........... A61B 2017/00526; A61B 2017/00862; A61B 2017/06028
USPC ........................................................ 606/223
See application file for complete search history.

(56) References Cited

U.S. PATENT DOCUMENTS

| | | | |
|---|---|---|---|
| 9,393,012 | B2 | 7/2016 | DiPiero |
| 10,039,568 | B2 | 8/2018 | Favier et al. |
| 2006/0047309 | A1* | 3/2006 | Cichocki, Jr. ..... A61B 17/06066 606/222 |
| 2007/0135838 | A1* | 6/2007 | Meyer ................... A61B 17/062 606/222 |
| 2007/0197981 | A1 | 8/2007 | Abe et al. |
| 2008/0140091 | A1* | 6/2008 | DeDeyne ........... A61B 17/0469 606/144 |
| 2013/0338709 | A1 | 12/2013 | Chang |
| 2014/0172015 | A1* | 6/2014 | Martin ............... A61B 17/0491 606/223 |
| 2014/0277109 | A1 | 9/2014 | Alshomer et al. |
| 2015/0190587 | A1* | 7/2015 | Peh ........................ A61B 90/80 604/164.04 |
| 2020/0268378 | A1 | 8/2020 | Cichocki, Jr. |
| 2020/0268379 | A1 | 8/2020 | Cichocki, Jr. |

FOREIGN PATENT DOCUMENTS

| | | |
|---|---|---|
| DE | 2203309 A1 | 8/1973 |
| DE | 2905398 A1 | 8/1980 |
| JP | 2013009914 A * | 1/2013 |
| WO | 2006027549 | 3/2006 |

OTHER PUBLICATIONS

Written Opinion of the International Searching Authority issued in corresponding International Application No. PCT/IB2021/052501, dated Aug. 17, 2021, 10 pages.

Invitation to Pay Additional Fees and, Where Applicable, Protest Fee including Communication Related to the Results of the Partial International Search, issued in corresponding International Application No. PCT/IB2021/052501, dated Jun. 25, 2021, 12 pages.

* cited by examiner

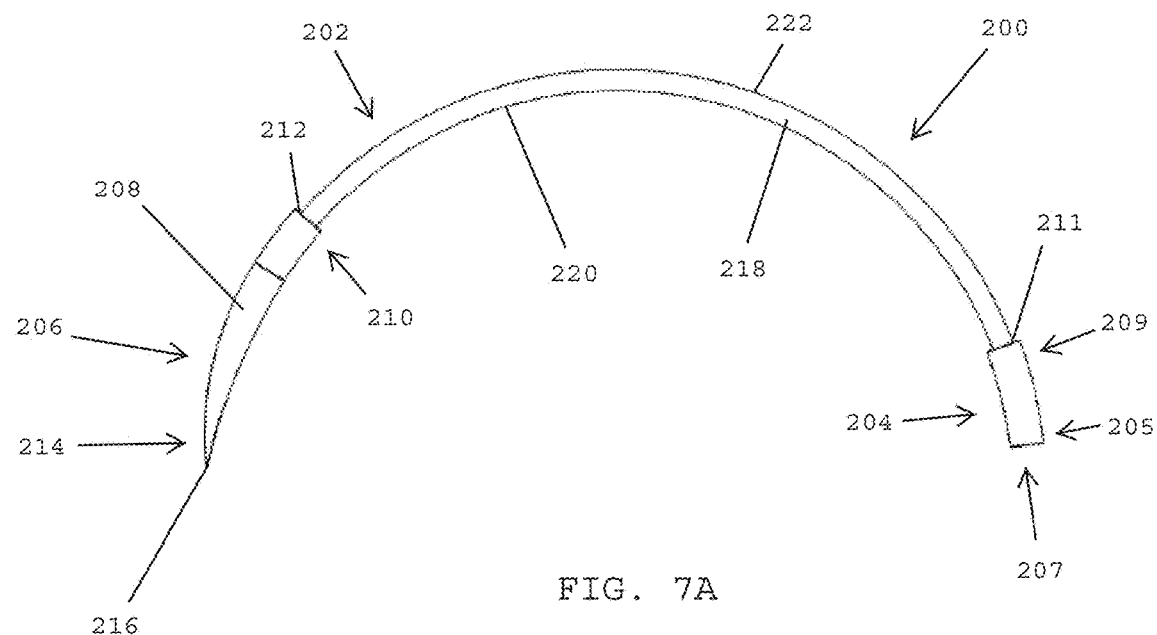
FIG. 7A
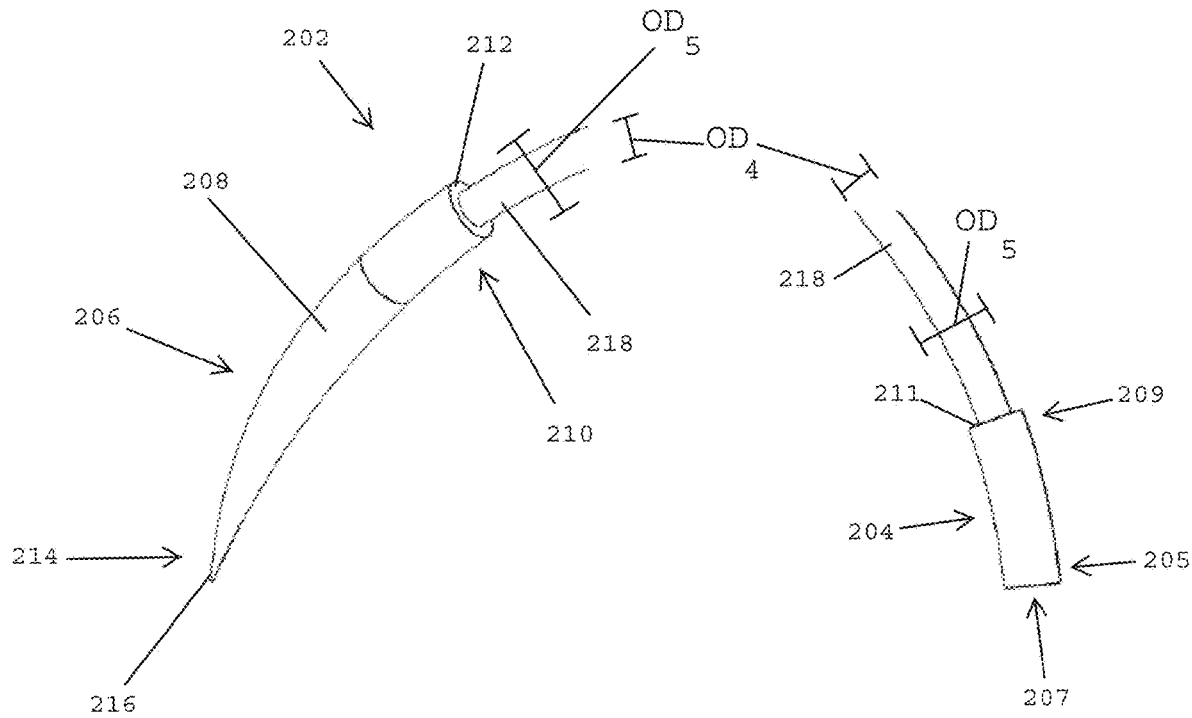
FIG. 7B
FIG. 7C

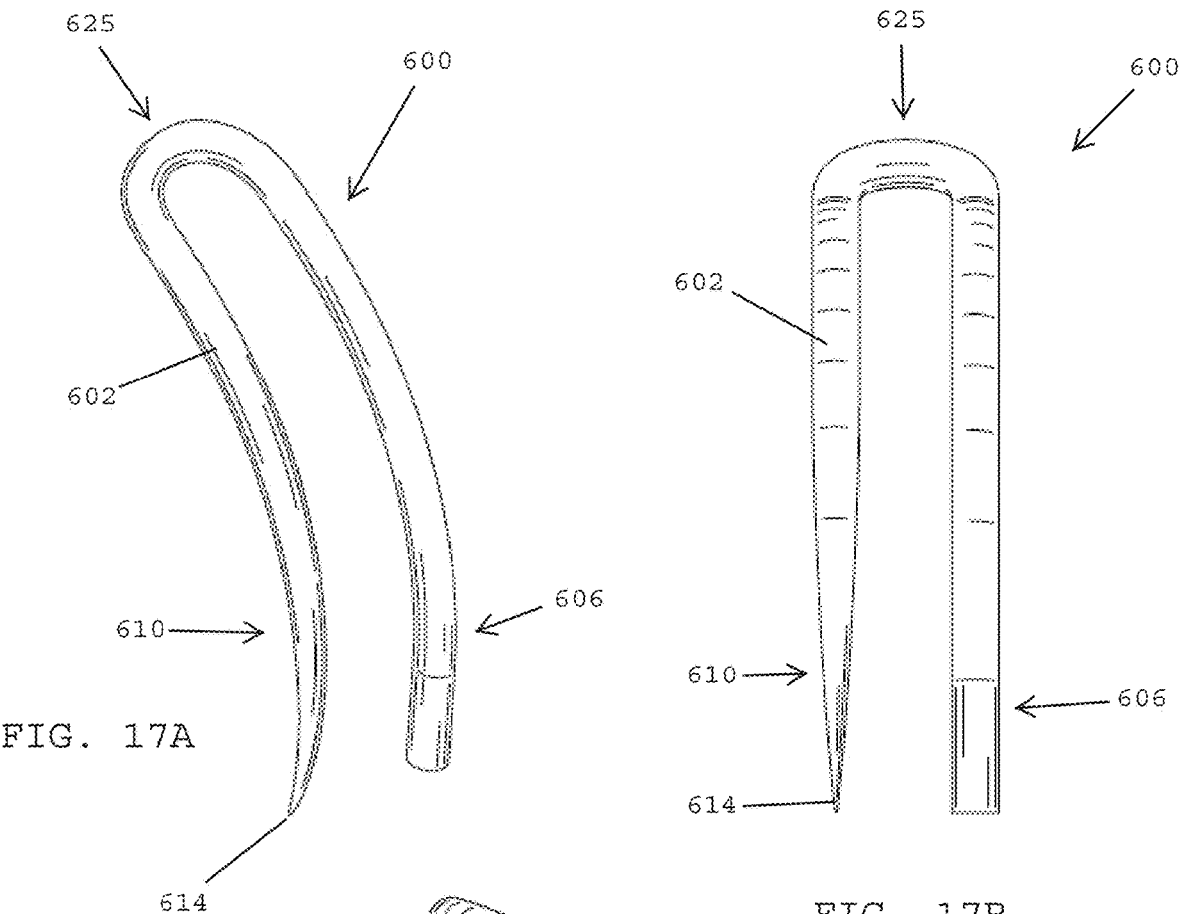
FIG. 17A
FIG. 17B
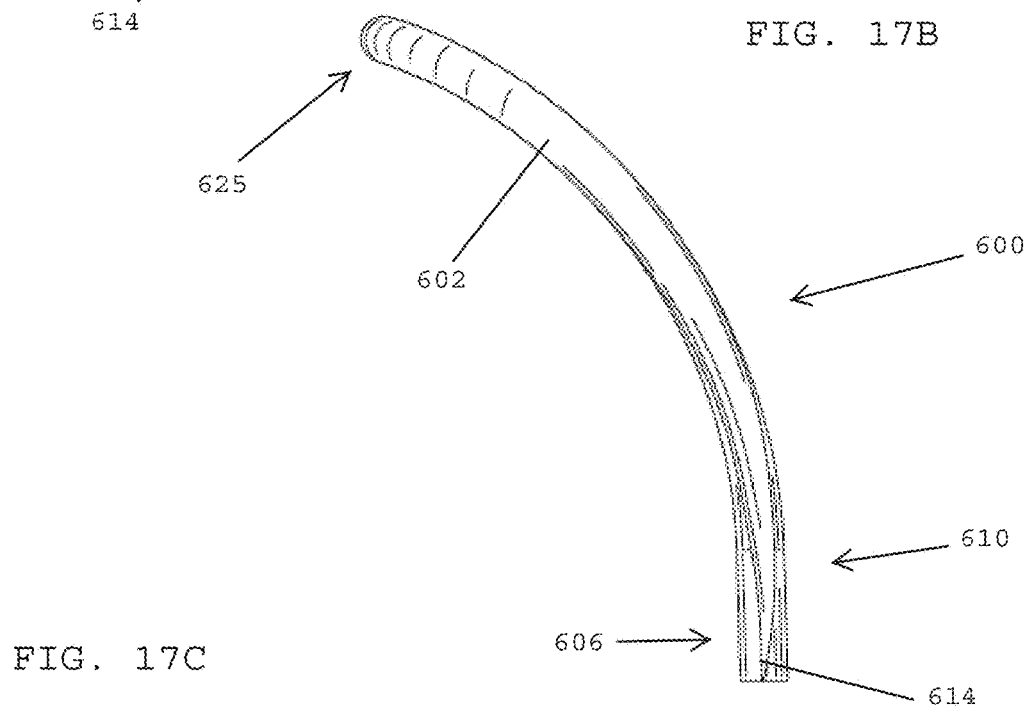
FIG. 17C

COMPOSITE SUTURE NEEDLES HAVING ELASTICALLY DEFORMABLE SECTIONS

BACKGROUND OF THE INVENTION

Field of the Invention

The present patent application is generally related to surgical procedures and surgical tools, and is more specifically related to systems, devices and methods of making and using elastic suture needles that are passed through lumens such as those associated with trocars and cannulas (hereinafter referred to as cannulas).

Description of the Related Art

Surgeons use lumens such as cannulas to position surgical tools, such as suture needles, at surgical sites. The size of a suture needle that can be passed through a cannula is limited by the size of the opening in the cannula. In many instances, surgeons desire to use larger curved suture needles (i.e., suture needles having a curvature are larger than the cannula opening can accommodate) for closing surgical wounds and repairing anatomical features, however, passing larger curved suture needles through smaller cannulas is difficult.

5 mm cannulas are often used during minimally invasive surgeries (MIS), however, surgeons cannot pass the larger suture needles through the 5 mm cannulas so they are forced to use only smaller suture needles. The smaller suture needles are less than optimal because, inter alia, they often require a surgeon to make many more passes of the suture needle and suture thread through tissue, which lengthens the surgical procedure and can frustrate the surgeon. Using smaller needles may also produce a bite distance that puts the wound or anatomical feature at risk of dehiscence.

Another drawback of using smaller suture needles is that larger sized sutures cannot be easily attached to the smaller suture needles. This often forces surgeons to use smaller sized sutures than are required for a suturing operation. Thus, when fine or smaller sized sutures are passed through tissue with a smaller bite size, a cheese wire effect may result, whereby the suture cuts through the tissue that it is intended to hold.

In an effort to resolve one or more of the above-noted problems, advances have been made to provide suture needles made of superelastic alloys having shape memory properties, which enable a curved suture needle to be straightened for being passed through a cannula. When the superelastic suture needle is removed from the other end of the cannula for use at a surgical site, the shape memory properties of the needle return it back to the original curved shape.

An alloy commonly referred to as nitinol is often used to make superelastic suture needles. Suture needles made of nitinol, however, can be very difficult to process, which results in high production costs that are often charged to customers, and which could substantially limit the adoption of nitinol suture needles for minimally invasive surgeries.

In addition, there are many challenges associated with securing sutures to the suture attachment barrels of nitinol suture needles. These challenges include the tendency of the suture attachment barrels of nitinol needles to spring back after a swaging step, which results in the formation of a weak attachment between the suture thread and the nitinol suture needle.

Thus, there remains a need for improved suture needles, which exhibit elasticity so that larger suture needles may be passed through relatively smaller cannulas (e.g., 5 mm cannulas) for use in surgical procedures. There also remains a need for suture needles that may be passed through smaller cannulas and not be plastically deformed. In addition, there is a need for systems, devices and methods of making larger suture needles made predominantly of stainless steels that can be elastically deformed for passing through the relatively smaller cannulas for use in minimally invasive surgery.

SUMMARY OF THE INVENTION

Introducing curved suture needles into a minimally invasive surgical field is challenging. When the curved suture needle is introduced through a device having a lumen, such as a cannula, the size of the curved suture needle is typically limited to a profile that is smaller than the inner diameter of the cannula. One way to introduce a larger needle through a smaller cannula is to flex or bend the needle into a profile that will fit within the inner diameter of the cannula. This typically results in the curved suture needle undergoing a degree of plastic deformation, however, which requires the suture needle to be re-shaped after it enters the surgical site and before it may be used in suturing.

Another approach is to fabricate a suture needle that is made entirely from a super-elastic material such as nitinol (i.e., a metal alloy made of nickel and titanium). In doing so, however, the resulting suture needle is not as strong as suture needles made from more commonly used materials (e.g., 455, 420, 300 series alloys or custom alloys such as tungsten-rhenium alloys), and thus the suture needle is not optimal for subsequent suturing procedures. Moreover, substantial challenges exist in the processing of nitinol alloy suture needles including point grinding, curve-setting, hole drilling, electro polishing and suture attachment. Attempts to overcome the above-identified challenges typically result in the production of poor quality and/or high cost suture needles.

Most materials can withstand a modest degree of strain before becoming plastically deformed. A highly elastic material (i.e. those alloys exhibiting a high Yield Strain) will withstand more strain, as compared to a less elastic material, before becoming plastically deformed. In one embodiment, a composite suture needle includes a highly elastic material at the greatest distances from the neutral axis, which will be able to withstand more flexing before becoming plastically deformed as compared to a suture needle made from a single, less elastic material having uniform elastic properties. This is because the outer diameter of the core material is smaller than the actual outer diameter of the composite suture needle.

In one embodiment of the present patent application, a suture needle may be manufactured, at least in part, from a core wire stock including a core section made of a strong alloy (e.g., stainless steels including martensitic-aged alloys such as ETHALLOY® Needle Alloy, or 455, 420, 300 or other custom alloys) and a second material having highly elastic properties (e.g., nitinol).

In one embodiment, the suture needle disclosed herein preferably has greater strength than a suture needle made entirely of a highly elastic material (e.g., nitinol), and the suture needle has a strength that entirely suitable for use in suturing tissue.

When a curved suture needle having a curved elongated body is flexed (e.g., flattened) for being passed through a cannula, the maximum bending takes place at a midsection of the curved elongated body that is located between the tissue-penetrating end and the suture attachment end. When flexing, the greatest strain takes place along an inner radial surface and an outer radial surface of the curved elongated body. The curved elongated body has a neutral axis that is near the center of the elongated body cross-section. There is no significant shear strain that occurs along the neutral axis, however, the degree of shear strain increases as the distance from the neutral axis increases.

In one embodiment, a composite suture needle having a large size and conventional curvature (e.g., having a semi-circular shape) may be passed through a lumen such as a cannula. The composite suture needle is elastically straightened as it is passed through the cannula and springs back to its original curvature upon being removed from an end of the cannula for use in surgery.

In one embodiment, the composite suture needle preferably includes an elongated body having a proximal end and a distal end with a pointed tip, and a sheath overlying the elongated body.

In one embodiment, the sheath includes a material that is more elastic than the elongated body.

In one embodiment, the elongated body and the sheath are curved.

In one embodiment, the pointed tip extends distally beyond a distal end of the sheath.

In one embodiment, the elongated body is made of a strong alloy such as stainless steel, and sheath is made of a highly elastic material such as nitinol.

In one embodiment, the stainless steel used to make the elongated body may include austenitic stainless steels, martensitic-aged (mar-aged) stainless steels, and stainless steels sold under the registered trademark ETHALLOY Needle Alloy.

In one embodiment, the elongated body preferably has a reduced diameter section that defines a first outer diameter and the distal end of the elongated body defines a second outer diameter that is greater in size than the first outer diameter of the reduced diameter section.

In one embodiment, the distal end of the elongated body includes a tapered section having a proximal end including a shoulder that defines the second outer diameter. In one embodiment, the tapered section preferably has a distal end that includes the pointed tip.

In one embodiment, the sheath has a proximal end, a distal end, and a lumen that extends from the proximal end to the distal end of the sheath. In one embodiment, the reduced diameter section of the elongated body is disposed within the lumen of the sheath. In one embodiment, the lumen of the sheath has an inner diameter that is greater than or equal to the first outer diameter of the reduced diameter section of the elongated body.

In one embodiment, the sheath has an outer surface that defines a third outer diameter that approximates the second outer diameter of the shoulder of the tapered section of the elongated body.

In one embodiment, a composite suture needle preferably includes an elongated body having a curved proximal body section, a curved distal body section, and a curved midsection that extends between the curved proximal body section and the curved distal body section. In one embodiment, the composite suture needle desirably includes a sheath overlying the curved midsection of the elongated body. The curved midsection of the elongated body is desirably made of a first material and the sheath is made of a second material that is more elastic than the first material of the curved midsection.

In one embodiment, the curved proximal section, the curved distal section, and the curved midsection of the elongated body form a unitary structure. In one embodiment, the curved proximal section, the curved distal section, and the curved midsection of the elongated body are made of the same material such as stainless steel.

In one embodiment, the curved midsection of the elongated body and the sheath overlying the curved midsection preferably define a flexible region of the composite suture needle that is more elastic than the curved proximal body section and the curved distal body section of the elongated body of the composite suture needle.

In one embodiment, the curved midsection of the elongated body is made of stainless steel and the sheath that overlies the curved midsection is made of a highly elastic material such as nitinol.

In one embodiment, the sheath preferably has a proximal end, a distal end, and a lumen that extends from the proximal end to the distal end of the sheath. In one embodiment, the curved midsection of the elongated body is disposed within the lumen of the sheath.

In one embodiment, the curved midsection of the elongated body has a first outer diameter and the lumen of the sheath has a first inner diameter that is greater than or equal to the first outer diameter of the curved midsection of the elongated body.

In one embodiment, the distal end of the curved proximal section and the proximal end of the curved distal section of the elongated body define a second outer diameter. In one embodiment, the sheath has an outer surface defining a third outer diameter that approximates the second outer diameter.

In one embodiment, the proximal body section of the elongated body preferably includes a proximal end face and a suture receiving hole is formed in the proximal end face.

In one embodiment, the curved distal body section of the elongated body includes a tissue piercing point at a distal end thereof.

In one embodiment, the sheath may be glued or welded to the curved midsection of the elongated body.

In one embodiment, a composite suture needle preferably includes a curved proximal body section made of stainless steel, a curved distal body section made of stainless steel, and a connector interconnecting the curved proximal and distal body sections.

In one embodiment, the connector is preferably made of a material that is more elastic than the stainless steel used to make the curved proximal and distal body sections.

In one embodiment, the connector interconnects a distal end of the curved proximal body section with a proximal end of the curved distal body section.

In one embodiment, the connector may include a dovetail structure for being connected with the distal end of the curved proximal body section and the proximal end of the curved distal body section.

In one embodiment, the connector preferably has an outer diameter that approximates an outer diameter of the distal end of the curved proximal body section and an outer diameter of the proximal end of the curved distal body section of the composite suture needle.

In one embodiment, the connector is made of nitinol and the stainless steel used for making the proximal and distal body sections may be austenitic stainless steels, martensitic-aged (mar-aged) stainless steels, and/or stainless steels sold under the registered trademark ETHALLOY Needle Alloy.

In one embodiment, the elongated body of the composite suture needle is curved along its length with one surface of the elongated body defining the concave aspect of the curve and another surface of the elongated body defining the convex aspect of the curve.

In one embodiment, a surgical method preferably includes passing the composite suture needle through a lumen of a cannula from the proximal end to the distal end of the cannula, whereby during the passing step the composite suture needle flattens out for transforming to a height that is less than or equal to the height of the lumen.

In one embodiment, after the passing step, the composite suture needle is preferably removed from the distal end of the cannula whereupon the composite suture needle transforms back to a curved shape having a height that is greater than the height of the lumen of the cannula.

In one embodiment, the composite suture needle may be elastically deformed to lower the height and/or the profile of the suture needle to pass the suture needle through a cannula, such as a cannula having a diameter of 5 mm or smaller.

In one embodiment, a needle driver may be used to secure a distal end of the composite suture needle with the suture attachment barrel of the composite suture needle trailing behind the tip of the composite suture needle. In one embodiment, the tip is preferably surrounded by clamping jaws at the distal end of a needle driver for protecting the tip as the composite suture needle is passed through a cannula. The clamping jaws preferably surround and protect the tip for preventing the tip from contacting the inside of the cannula as it is passed through the cannula, thereby avoiding damage to the tip during its passage through the cannula.

In one embodiment, when the composite suture needle is held by the needle driver, the tip of the composite suture needle does not extend or protrude outside the external surface of the needle holder.

In the case of suture needles made of 420 alloys, forming a hole by mechanical drilling may be successfully completed using conventional methods because the core wire is the same as the needle wire that is currently being drilled.

In one embodiment, the core alloy may be chemically leached or electropolished to a specified depth at the proximal end of the needle to produce a hole for suture needle attachment while leaving the more chemically inert nitinol outer shell intact, which may be especially applicable when using high strength martensitic-aged alloys and the like as a core material.

In one embodiment, grinding the point end and/or forming cutting edges may be easier since the point end is made from the core wire material, and not the super elastic material (e.g., not nitinol).

In one embodiment, curve setting may be facilitated since the core alloy will enable the needle to be curved with conventional curving equipment used in the art of suture needle manufacture. By allowing the core alloy to plastically deform in the curving process, it provides a resistance to the nitinol that has a propensity to straighten back to its original form after conventional curving methods have been applied.

In one embodiment, the suture needles may be gathered in bulk and efficiently routed through a shape setting heat cycle, thus obviating the need for heat setting fixtures and additional handling required to shape-set monolithic nitinol alloy needles.

In one embodiment, when a needle needs to be flexed for being passed through a cannula, the maximum bending takes place between the tissue-penetrating end and the suture attachment end (i.e., the midsection). When flexing, the greatest strain takes place along the inner radius surface and the opposing outer radius surface.

In one embodiment, a method of making a composite suture needle preferably includes obtaining a length of core wire made from a suitable material for use in the fabrication of suture needles. The core wire preferably includes an outer diameter, a first end and a second distal end.

In one embodiment, the method preferably includes obtaining an outer sheath (e.g., a sleeve, tubing) of similar or shorter length as the length of the core wire. The sheath preferably has a proximal end and a distal end.

In one embodiment, the sheath preferably has an inner diameter that is slightly larger than the outer diameter of the core wire, and an outer diameter approximating the desired finished outer diameter of the composite suture needle.

In one embodiment, a length of core wire is placed inside the sheath for aligning the proximal end of the core wire with the proximal end of the sleeve.

In one embodiment, the sheath may be fixed to the core wire using a thermal shrink fit process. In one embodiment, the sheath may be heated to thermally expand the diameter of the sheath to enable the sheath to slide over the core wire (e.g., an elongated body made of stainless steel). After the sheath is positioned over the core wire, the sheath may cool to thermally contract the diameter of the sheath to hug or snuggly fit over the core wire, thereby forming a composite suture needle having a flexible region that is covered by the sheath.

In one embodiment, the sheath may be affixed to the core wire by applying an adhesive in the space between the outer diameter of the core wire and inner diameter of the sheath.

In one embodiment, the sheath may be affixed to the core wire by using a linking material between the outer diameter of the core wire and the inner diameter of the sheath, whereby the linking material is weldable to both the core wire material and the sheath material.

In one embodiment, a hole for receiving a suture may be formed in the composite suture needle by drilling the core material at the proximal end of the composite suture needle, or especially for high strength mar-arged alloys, electrochemically etching/leaching the core wire to a specified depth to produce a symmetrical suture receiving hole.

In one embodiment, the distal end of the core wire may be ground (or material may be removed) from the distal end of the composite structure to form a point at the distal end of the composite suture needle.

In one embodiment, a composite suture needle may have a stainless steel core and a connector component made of a highly elastic material that is only present along the inner radius surface and the opposing outer radius surface of the suture needle. The mating of the highly elastic connector component to the conventional suture needle material of the core may be achieved in a similar manner as the sheath or sleeve configuration (e.g., affixing, gluing, or welding). In one embodiment, however, the highly elastic connector component may include a mechanical attachment structure, such as a dovetail joining component.

In one embodiment, the composite suture needle may be curved with equipment and methods known in the art, to produce a free-standing composite suture needle having a steel core and a nitinol sheath that may be subsequently thermally treated to shape set the outer nitinol sleeve component without the need for fixtures or elaborate additional processes.

In one embodiment, where the core material of the composite suture needle is a martensitic-aged alloy, the shape setting and precipitation strengthening heat treatment steps may be conducted at the same time (e.g., at 480 degrees C. or higher for two or more minutes).

In one embodiment, a method of making a composite suture needle preferably includes obtaining a length of core wire made from a suitable material for use in the fabrication of suture needles, the core wire having an outer diameter, a proximal end and a distal end, and forming a thin strip of nitinol around the steel core wire by simultaneously pulling the steel core wire and the nitinol strip through a series of reducing dies suitable for the manufacture of round tubing.

In one embodiment, as the nitinol tube is formed around the steel core through the progression of die drawing steps, a seam of the nitinol may be welded via laser or micro-TIG welding techniques.

In one embodiment, the elastic sheath may be shorter than the core wire.

In one embodiment, the composite suture needle may be mechanically drilled and/or laser drilled for forming suture receiving holes.

In one embodiment, the suture receiving hole may be chemically or electrochemically formed by etching away the core material.

In one embodiment, the composite suture needles may be curved to a specified free-standing shape and then heat treated in bulk to complete the shape setting process.

These and other preferred embodiments of the present patent application will be described in more detail below.

BRIEF DESCRIPTION OF THE DRAWINGS

FIG. 1C-1 is a magnified cross-sectional view of a mid-section of the suture needle shown in FIG. 1C.

FIG. 7A is a side view of an elongated body of a composite suture needle, in accordance with one embodiment of the present patent application.

FIG. 7B is a magnified view of a distal end of the elongated body shown in FIG. 7A.

FIG. 7C is a magnified view of a proximal end of the elongated body shown in FIG. 7A.

FIG. 17A shows a perspective view of a composite suture needle having a highly elastic midsection for enabling the composite suture needle to be moved into a bent configuration for being passed through a cannula, in accordance with one embodiment of the present patent application.

FIG. 17B shows an end view of the composite suture needle shown in FIG. 17A.

FIG. 17C shows a side view of the composite suture needle shown in FIGS. 17A and 17B.

DETAILED DESCRIPTION OF PREFERRED EMBODIMENTS

Figure 1A:
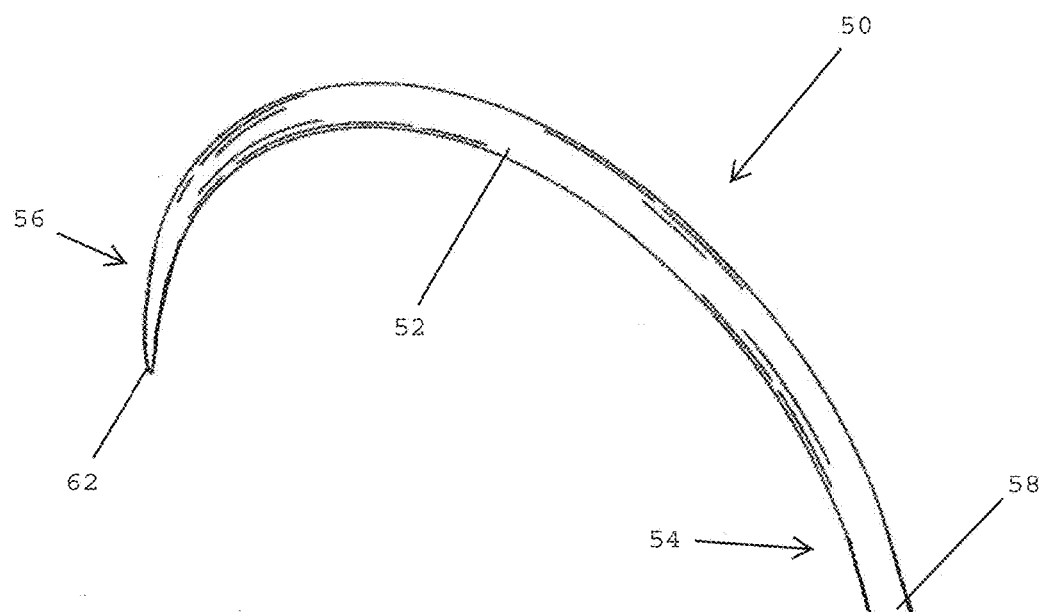
FIG. 1A is a perspective view of a suture needle.
Figure 1B:
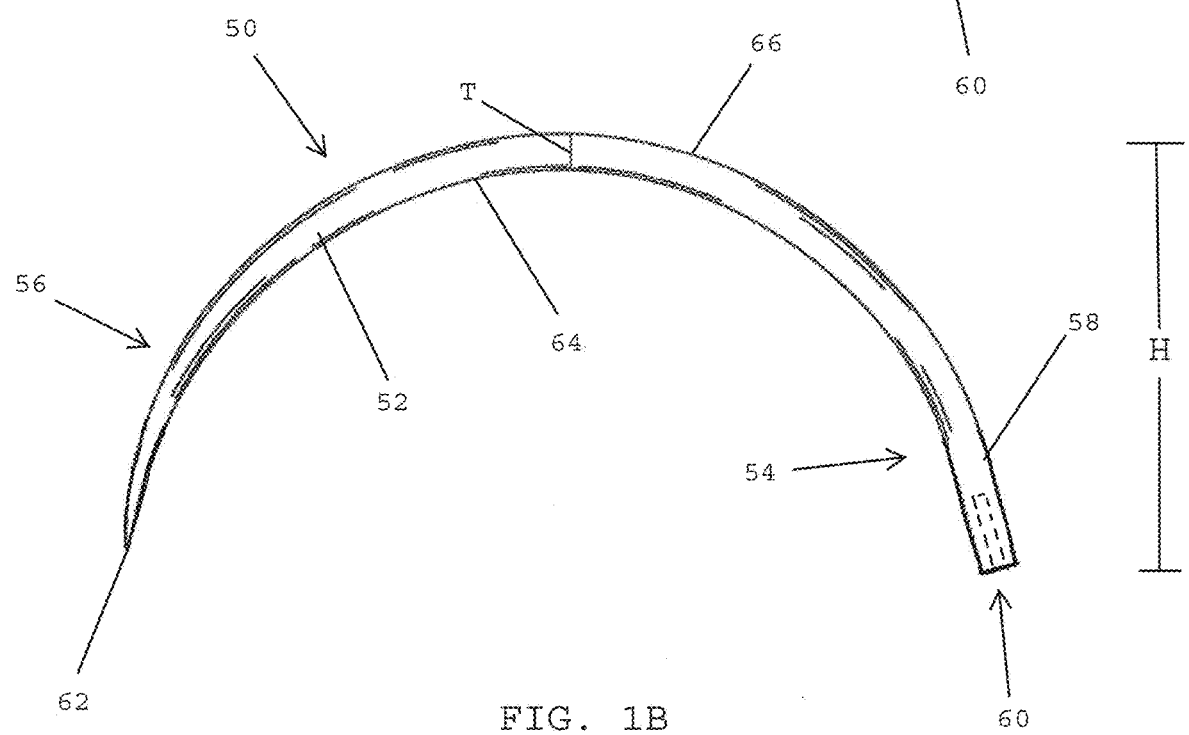
FIG. 1B is a side elevation view of the suture needle shown in FIG. 1A.
Figure 1C:
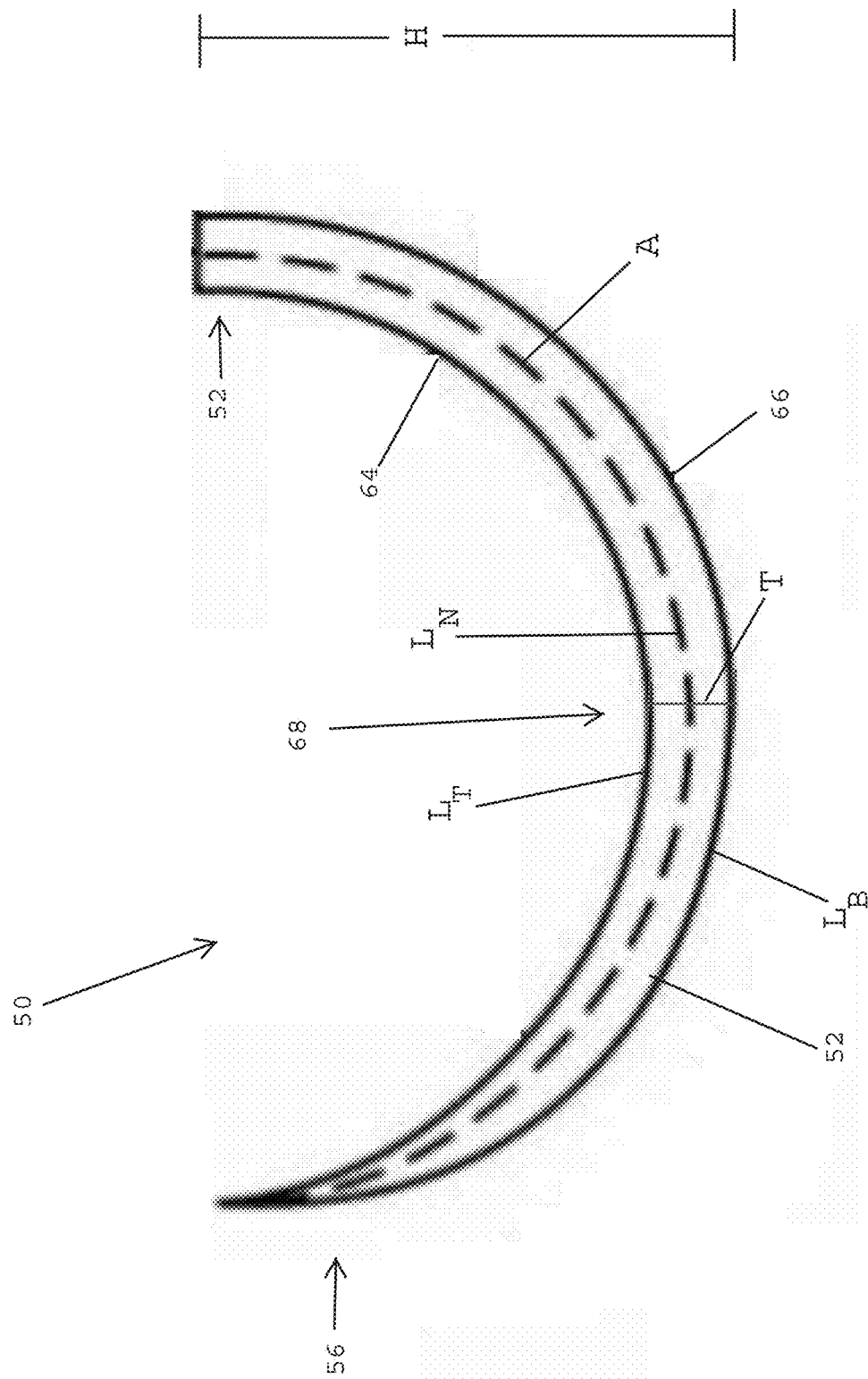
FIG. 1C is a schematic view of the suture needle shown in FIGS. 1A and 1B.

FIGS. 1A-1C show a conventional suture needle 50 having an elongated body 52 with a proximal end 54 and a distal end 56. The elongated body 52 of the suture needle 50 is curved and has a half circle or semi-circular shape.

The suture needle 50 includes a suture attachment barrel 58 that is adjacent the proximal end 54 of the elongated body 52, and a suture attachment opening 60 that is formed in a proximal face of the suture attachment barrel. An end of a surgical suture (e.g., a filamentary element) is inserted into the suture attachment opening 60 and the suture attachment barrel 58 is swaged for securing the end of the surgical suture to the suture attachment barrel 58 of the elongated body 52 of the suture needle 50.

The suture needle 50 includes a tip 62, such as a sharpened or pointed tip, that is integral to the distal end 56 of the elongated body 52 and that defines a leading or distal-most end of the suture needle 50. The tip 62 is sharpened for piercing tissue to facilitate passing the distal end 56 of the elongated body 52 of the suture needle 50 through tissue during a suturing operation.

Referring to FIGS. 1B and 1C, the elongated body 52 of the suture needle 50 includes an inner radial surface 64 that extends along the inside of the curve of the curved elongated body 52 (i.e., the concave curved surface), and an outer radial surface 66 that extends along the outside of the curve of the curved elongated body 52 (i.e., the convexly curved surface). The inner and outer radial surfaces 64, 66 of the elongated body 52 define the thickness T of the elongated body 52 of the suture needle 50, whereby the axis for measuring the thickness T of the elongated body is perpendicular to the neutral axis A of the elongated body 52 of the suture needle 50.

When the suture needle 50 is in its original, half-circle configuration, the elongated body 52 of the suture needle 50 defines a height H. When external forces are exerted upon the outer surfaces of the elongated body 52 of the suture needle 50 (e.g., when passing the suture needle through the lumen of a cannula), the elongated body will flex, bend, straighten, and/or flatten out for transforming into an elongated body having a lower height or profile than the original height H.

Figures 1, 1C:
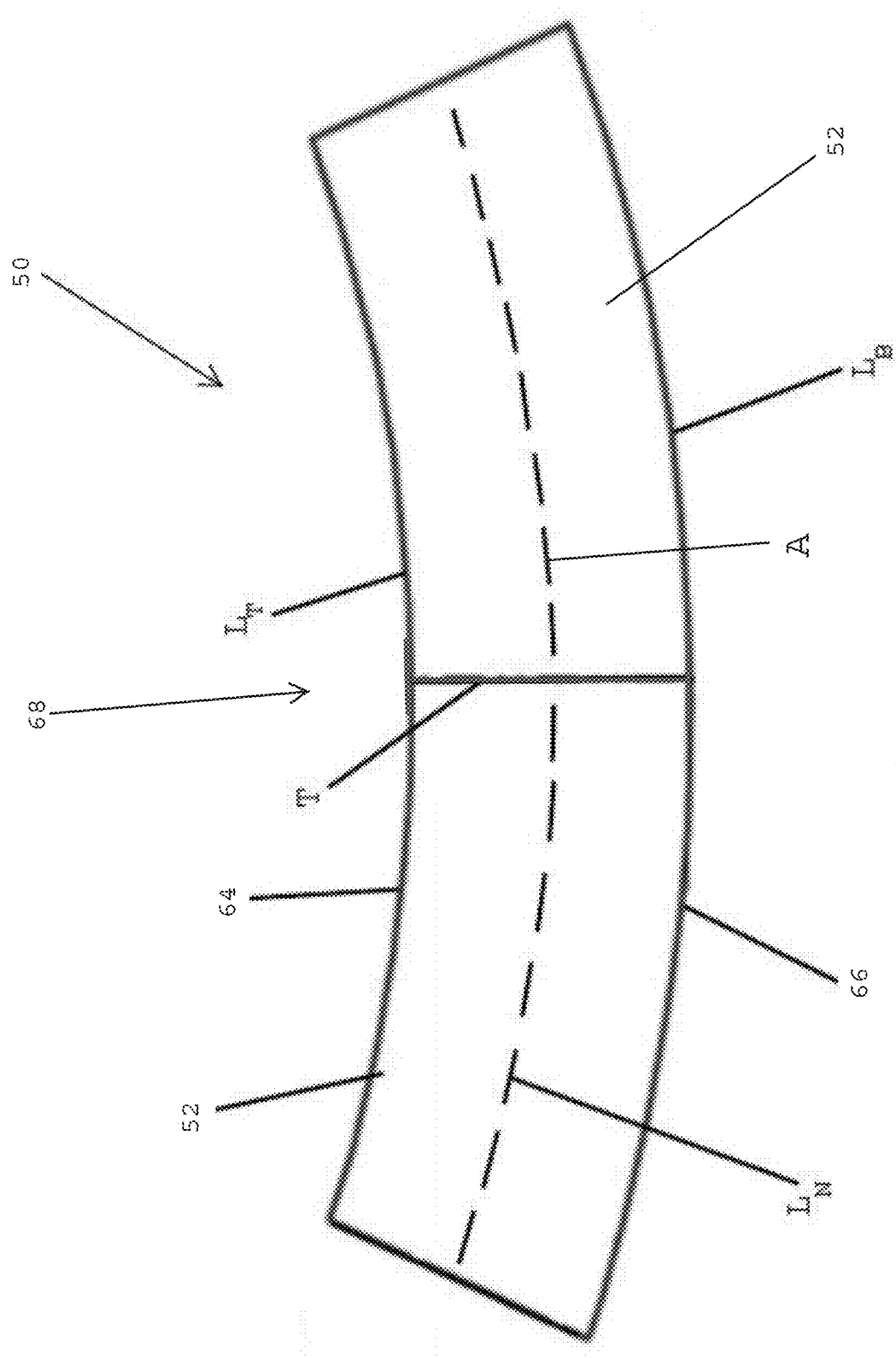

Referring to FIGS. 1C and 1C-1, the elongated body 52 of the suture needle 50 has a length $L_N$ extending along the neutral axis A of the elongated body 52. The neutral axis $L_N$ extends between the proximal end 54 and the distal end 56 of the elongated body 52, which is also referred to as the neutral length of the suture needle 50. The elongated body 52 of the suture needle 50 has a top length $L_T$ that extends along the inner radial surface 64 of the elongated body 52 between the proximal end 54 and the distal end 56 of the elongated body, and a bottom length $L_B$ that extends along the outer radial surface 66 of the elongated body 52 between the proximal end 54 and the distal end 56 of the elongated body 52.

Referring to FIG. 1C-1, when a midsection 68 of the elongated body 52 of the suture needle 50 is straightened for being passed through a cannula, tension and compression forces are applied at the respective inner and outer surfaces 64, 66 of the elongated body 52 of the suture needle 50. When the midsection 68 of the elongated body 52 is straightened, the inner radial surface 64 of the elongated body 52 is under tension, and the outer radial surface 66 of the elongated body 52 is under compression. The part of the elongated body 52 that extends along the neutral axis A that defines the neutral length $L_N$ of the elongated body 52 is under neither tension nor compression. The elastic strain calculation associated with transforming the half circle suture needle (shown in FIGS. 1A-1C and 1C-1) to a straightened configuration may be calculated using the equation $\varepsilon = \Delta L / L_N$, where $\Delta L$ is the change in the top length $L_T$ of the suture needle at the inner radial surface 64 of the elongated body 52 or the change in the bottom length $L_B$ of the suture needle at the outer radial surface 66 of the elongated body 52, and $L_N$ is the neutral length of the elongated body of the suture needle that is mid-way between the inner and outer radial surfaces 64, 66 of the elongated body.

When the suture needle 50 is flexed for being passed through the lumen of a cannula, the maximum bending takes place at the midsection 68 of the elongated body 52. When flexing, the greatest strain takes place along the inner radial surface 64 and the outer radial surface 66 of the elongated body 52. The neutral axis A that extends along the neutral length $L_N$ is near the center of the cross-section of the elongated body. During flexing (e.g., straightening) of the elongated body, there is no shear strain that occurs along the neutral axis A that extends along the neutral length $L_N$ of the elongated body 52. The degree of strain increases, however, as the distance from the neutral axis $L_N$ increases. Thus, during flexing of the suture needle 50, the shear strain is greater at the inner and outer radial surfaces 64, 66 and lower or negligible along the neutral length $L_N$.

In one embodiment, a composite suture needle preferably includes a core component made of a first material and a second component made of a second material that is more elastic than the first material. In one embodiment, the first component may include a core component made of stainless steel, and the second component may include an outer sheath made of a highly elastic material (e.g., nitinol) that covers a section of the core component.

Figure 2A:
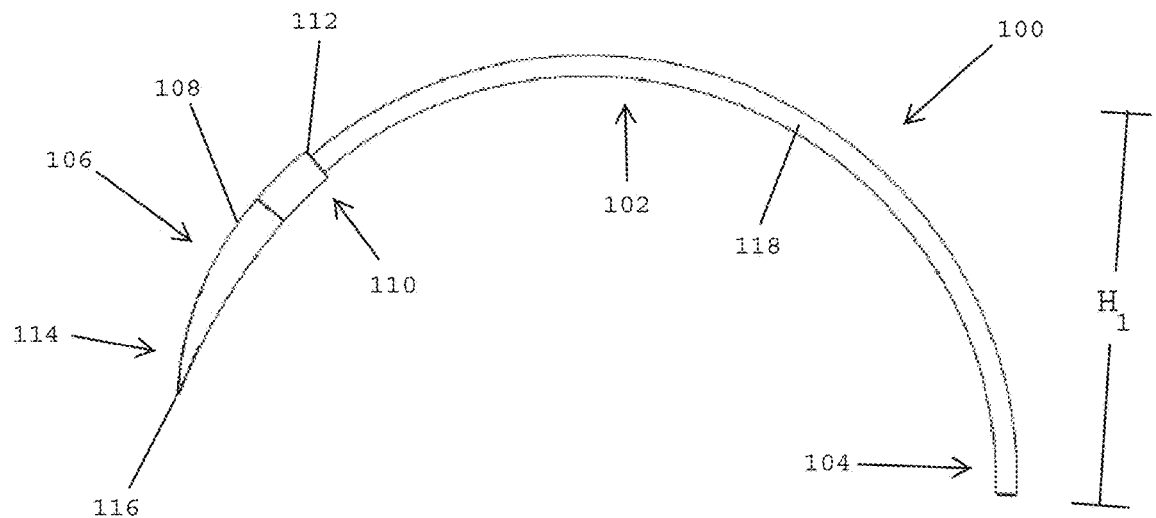
FIG. 2A is a side view of an elongated body of a composite suture needle, in accordance with one embodiment of the present patent application.
Figure 2B:
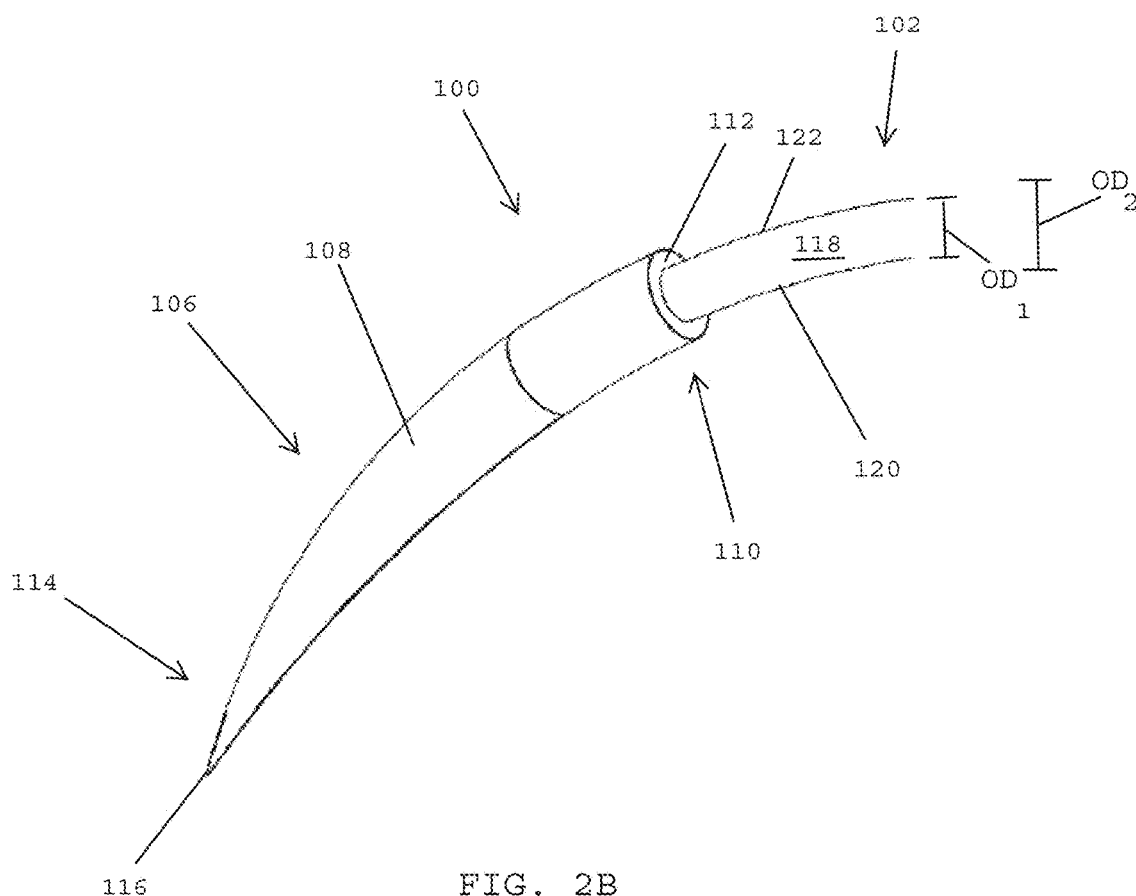
FIG. 2B is a magnified view of a distal end of the elongated body shown in FIG. 2A.

Referring to FIGS. 2A and 2B, in one embodiment, a composite suture needle 100 preferably includes an elongated body 102 (i.e., the core component) having a proximal end 104 and a distal end 106. In one embodiment, the distal end 106 of the elongated body 102 preferably includes a tapered section 108 having a proximal end 110 that defines a shoulder 112 and a distal end 114 that includes a sharpened or pointed tip 116. The tapered section 108 preferably tapers inwardly between the proximal end 110 and the distal end 114 thereof. In one embodiment, the pointed tip 116 at the distal end 114 of the tapered section 108 preferably defines a leading end of the elongated body 102, which is designed for piercing tissue to facilitate passing the distal end 106 of the elongated body 102 through tissue during a suturing operation.

In one embodiment, the elongated body 102 of the composite suture needle 100 preferably includes a reduced diameter section 118 that extends between the proximal end 104 of the elongated body and the larger diameter shoulder 112 of the tapered section 108. In one embodiment, the reduced diameter section 118 has a cross-section having a circular shape, which is configured to receive a sheath made of a highly elastic material, as will be described in more detail herein.

Referring to FIG. 2B, in one embodiment, the reduced diameter section 118 of the elongated body 102 preferably defines a first outer diameter $OD_1$ and the shoulder 112 of the tapered section 108 preferably defines a second outer diameter $OD_2$ that is greater than the first outer diameter $OD_1$ of the reduced diameter section 118 of the elongated body 102.

Referring to FIGS. 2A and 2B, in one embodiment, the elongated body 102 may be curved and/or may have a half circle or semi-circular shape. In one embodiment, the reduced diameter section 118 of the elongated body 102 is curved and preferably includes a concave surface 120 that extends along the inside of the curve of the reduced diameter section and a convexly curved outer surface 122 that extends along the outside of the curve of the reduced diameter section 118. The elongated body 102 preferably defines a first height $H_1$.

In one embodiment, the elongated body 102 may be made of strong alloys such as stainless steels. In one embodiment, the stainless steels may include austenitic stainless steels (302SS), and martensitic-aged (mar-aged) stainless steels (455SS).

The austenitic stainless steels (302SS) may possess austenite as their primary crystalline structure. The austenite crystalline structure is achieved by sufficient additions of the austenite stabilizing elements nickel, manganese and nitrogen. Due to their crystalline structure austenitic steels are not hardenable by heat treatment. See https://en.wikipedia.org/wiki/Austenitic_stainless_steel. Nevertheless, exceptionally high strength may be achieved via work hardening especially in the wire drawing process used to produce feedstock for needle manufacturing.

The martensitic-aged (mar-aged) stainless steels (455SS) are preferably steels that are known for possessing superior strength and toughness without losing malleability. The "aging" portion of the word Mar-aged refers to the extended heat-treatment process. These steels are a special class of low-carbon, ultra-high-strength steels that derive their strength not from carbon, but from precipitation of intermetallic compounds. Typically, the principal alloying element is 7 to 25 wt. % nickel. Secondary alloying elements, which include titanium and copper, are added to produce intermetallic precipitates. See https://www.asminternational.org/c/portal/pdf/download?articleId=AMP16909P30&groupId=10192

One type of martensitic-aged alloy that was specifically developed for suture needles and that provides levels of strength far exceeding that of alloys previously used for making suture needles is sold under the registered trademark ETHALLOY Needle Alloy. The ETHALLOY Needle Alloy is strengthened by a combination of work hardening and thermal processing (precipitation strengthening).

Figure 3A:
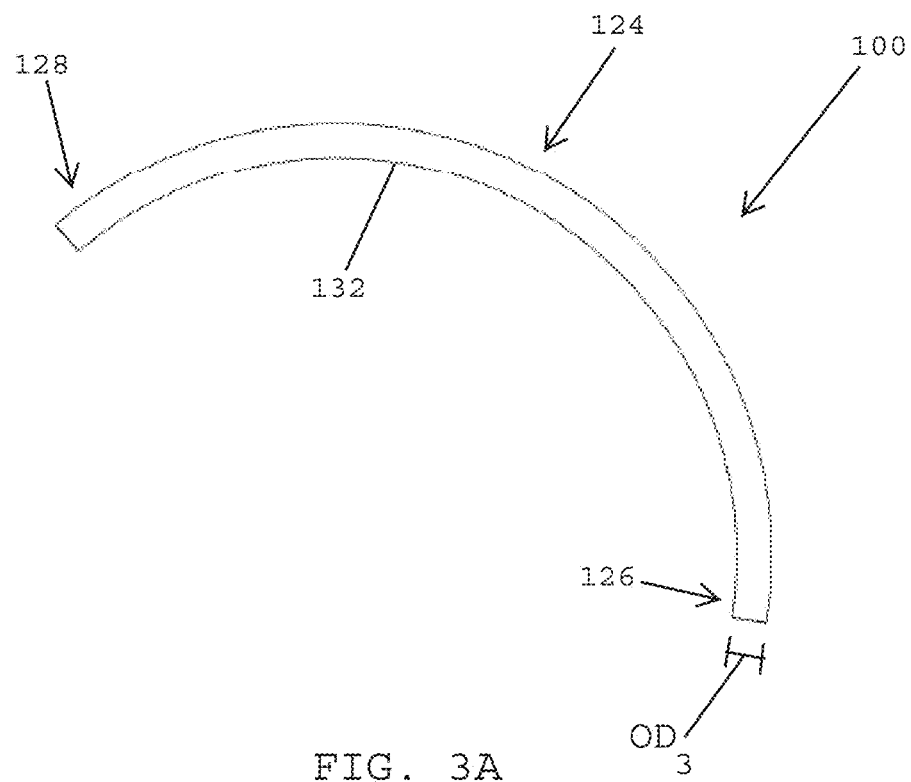
FIG. 3A is a side view of a sheath of a composite suture needle, in accordance with one embodiment of the present patent application.
Figure 3B:
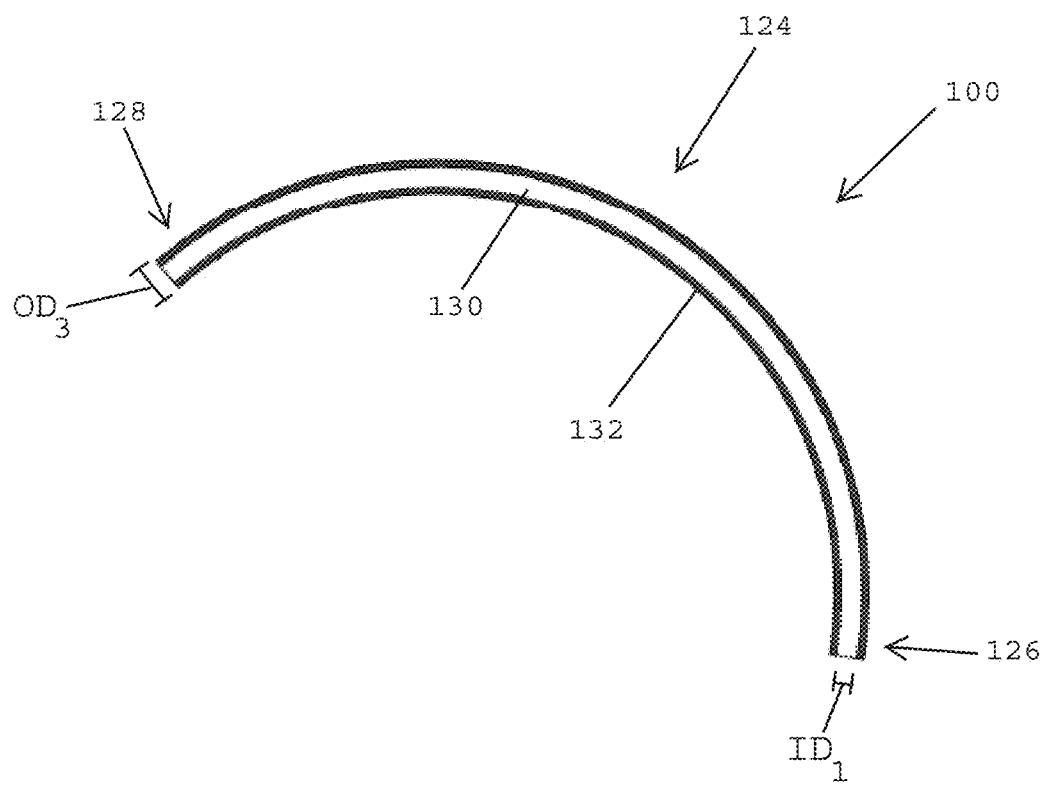
FIG. 3B is a cross-sectional view of the sheath shown in FIG. 3A.

Referring to FIGS. 3A and 3B, in one embodiment, a composite suture needle 100 preferably includes a sheath 124 made of a material having higher level of elasticity than the material used to make the elongated body 102 (FIGS. 2A and 2B) of the composite suture needle. In one embodiment, the sheath 124 may be made of a highly elastic material such as nitinol. In one embodiment, the sheath 124 may have a sleeve, tubular, or cylindrical shape. In one embodiment, the sheath 124 is preferably sized, shaped and/or configured to be assembled over the reduced diameter section 118 of the elongated body 102 (FIGS. 2A and 2B) to form the composite suture needle 100 including the elongated body, which is relatively less elastic, and the sheath 124, which is relatively more elastic than the material used to make the elongated body.

In one embodiment, the sheath 124 preferably has a proximal end 126, a distal end 128, and a lumen 130 that extends from the proximal end 132 to the distal end 134 thereof. Referring to FIGS. 2B and 3B, in one embodiment, the lumen 136 of the sheath 124 desirably defines an inner diameter $ID_1$ that is slightly larger than the outer diameter $OD_1$ of the reduced diameter section 118 of the elongated body 102. In one embodiment, the sheath 124 has an outer surface 132 that preferably defines an outer diameter $OD_3$ that approximates the outer diameter $OD_2$ of the shoulder 112 of the tapered section 108 of the elongated body 102. In one embodiment, when the sheath 124 is assembled over the reduced diameter section 118 of the elongated body to form a composite needle 100, the distal end 128 of the sheath 124 preferably abuts against the shoulder 112 of the tapered section 108 of the elongated body 102. In one embodiment, the outer surface 132 of the sheath 124 approximates the outer surface at the proximal end 110 of the tapered section 108 of the elongated body to provide a smooth transition between the tapered section 108 and the sheath 124 of the composite suture needle.

In one embodiment, the sheath desirably covers most of the length of the elongated body. In one embodiment, the proximal end of the sheath preferably extends proximally beyond the proximal end of the elongated body to provide a suture receiving hole. In one embodiment, the sheath may be slid over the elongated body to form a thermal fit and/or a compression fit between the sheath and the elongated body.

Figure 4A:
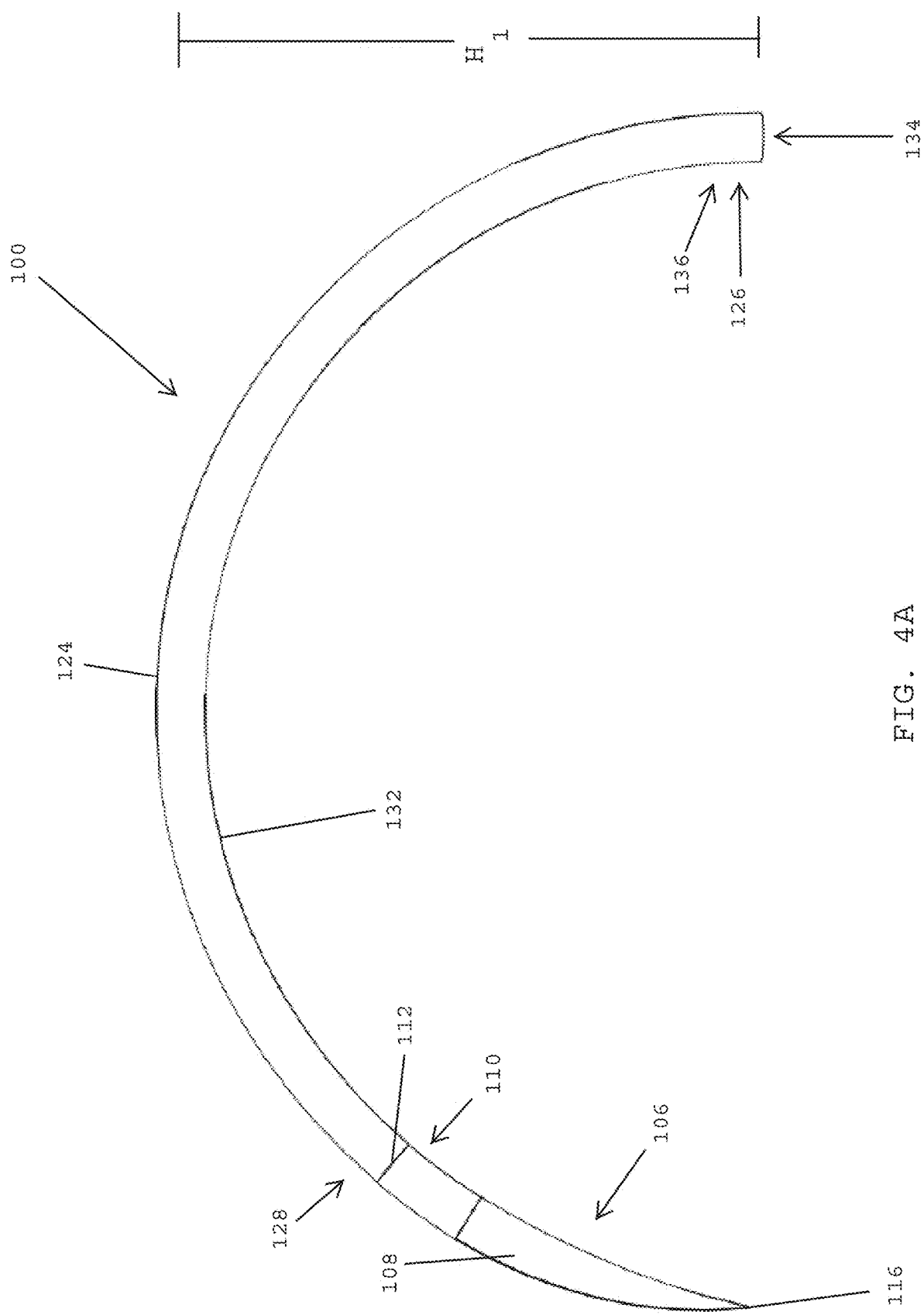
FIG. 4A is a side view of a composite suture needle including the sheath of FIGS. 3A and 3B assembled with the elongated body of FIGS. 2A and 2B, in accordance with one embodiment of the present patent application.
Figure 4B:
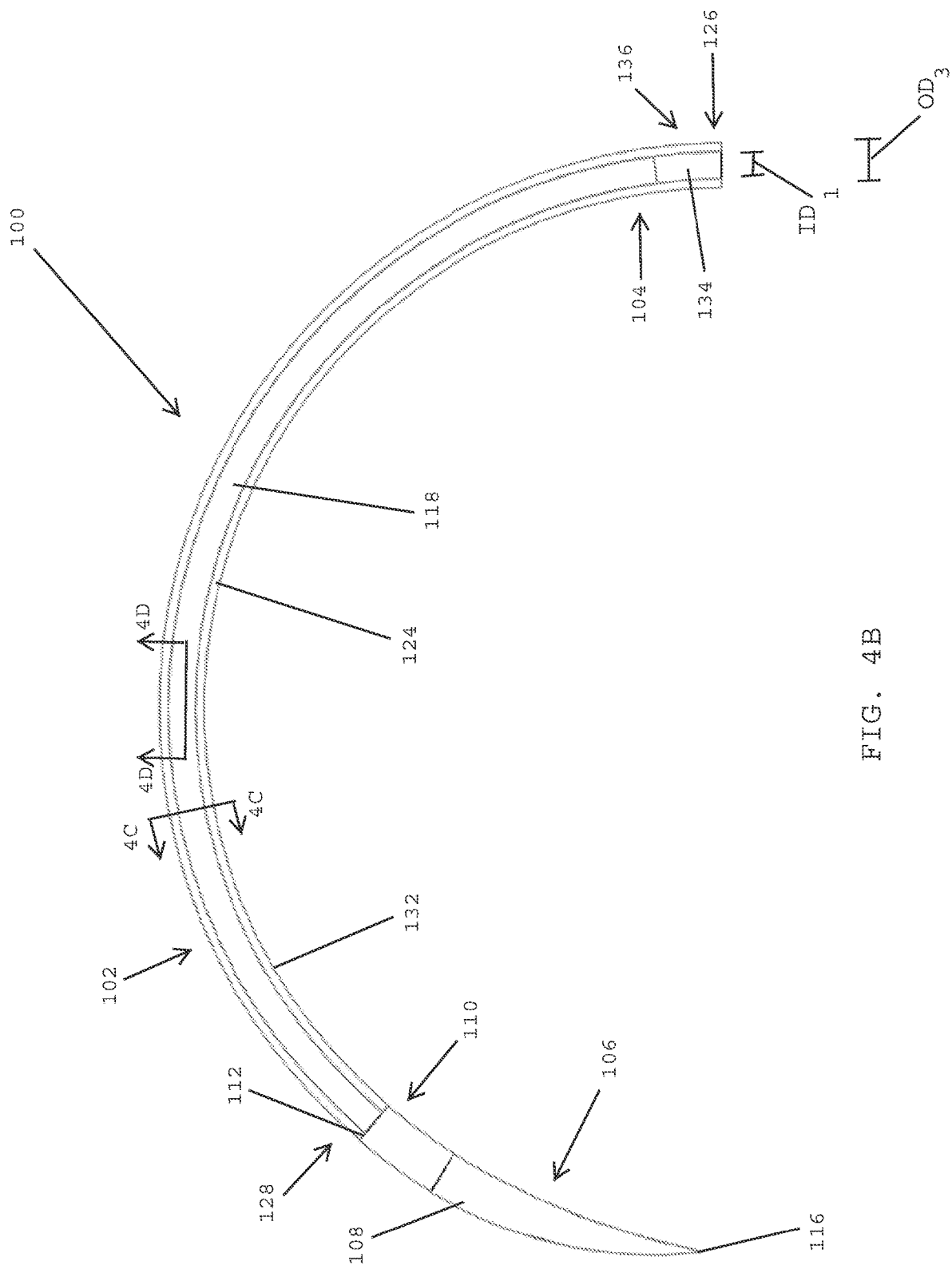
FIG. 4B is a cross-sectional view of the composite suture needle shown in FIG. 4A.

Referring to FIGS. 4A and 4B, in one embodiment, the composite suture needle 100 may be formed by assembling the sheath 124 over the reduced diameter section 118 of the elongated body 102. In one embodiment, the distal end 128 of the sheath 124 preferably abuts against the shoulder 112 (FIG. 2B) of the tapered section 108 of the elongated body 102. The inner diameter $ID_1$ of the sheath 124 is preferably slightly larger than the outer diameter $OD_1$ (FIG. 2B) of the reduced diameter section 118 of the elongated body 102. The outer surface 132 of the sheath 124 preferably defines an outer diameter $OD_3$ (FIG. 3B) that approximates the outer diameter at the proximal end 110 of the tapered section 108 of the elongated body 102.

In one embodiment, after the sheath 124 has been assembled over the reduced diameter section 118 of the elongated body 102, the proximal end 126 of the sheath 124 preferably extends proximally beyond the proximal end 104 of the elongated body 102 to define a suture attachment opening 134 that is located at the proximal end of the composite suture needle 100. The suture attachment opening 134 is preferably surrounded by a swage zone 136 of the sheath 124 that may be swaged or crimped for securing an end of a suture thread to the proximal end of the composite suture needle 100. In one embodiment, an end of a suture thread (not shown) may be inserted into the suture attachment opening 134 of the sheath 124 and the swage zone 136 of the sheath 124 may be swaged for securing the end of the suture thread to the proximal end of the composite suture needle 100.

Figure 4C:
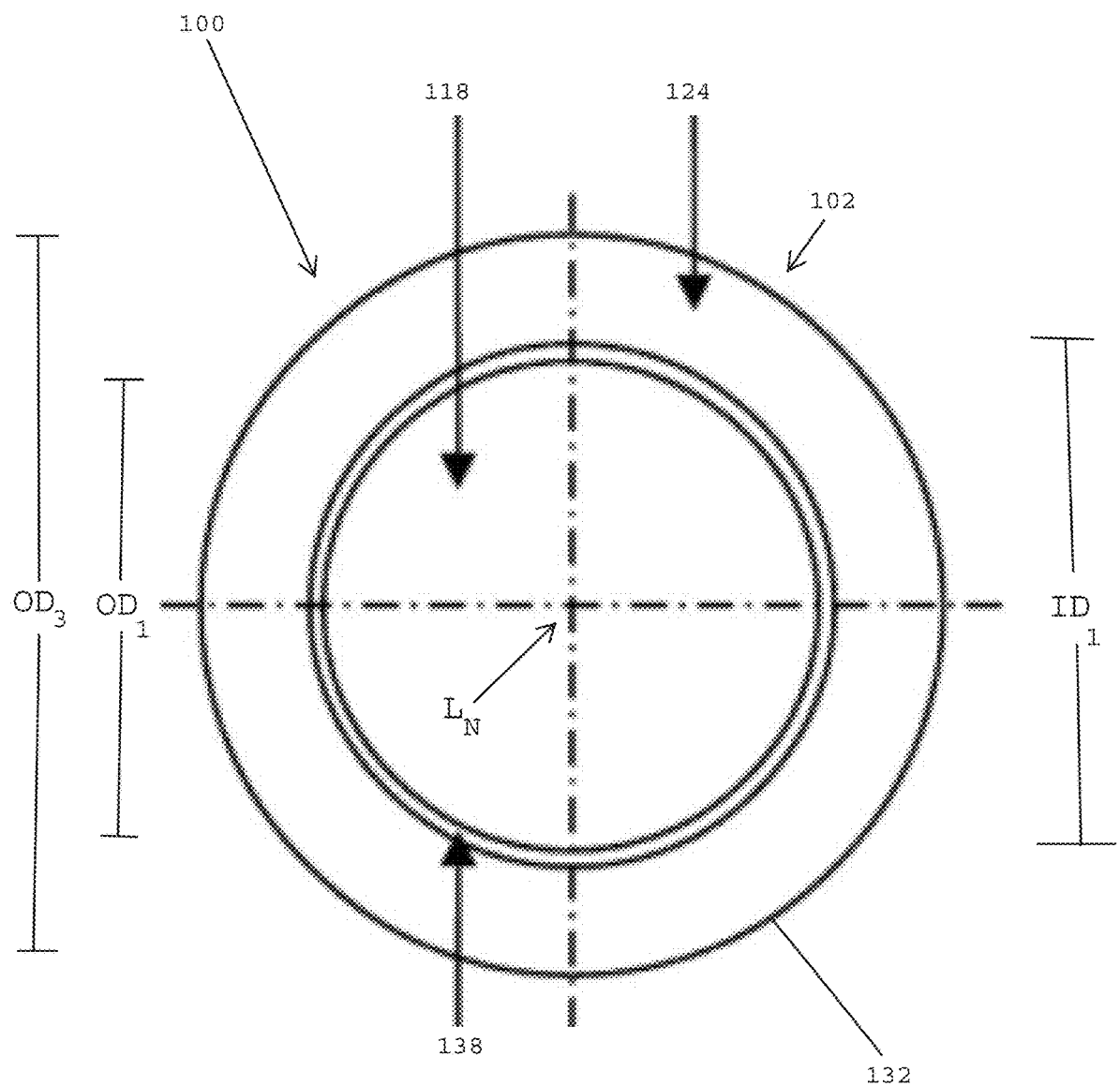
FIG. 4C is another cross-sectional view of the composite suture needle of FIG. 4A.
Figure 4D:
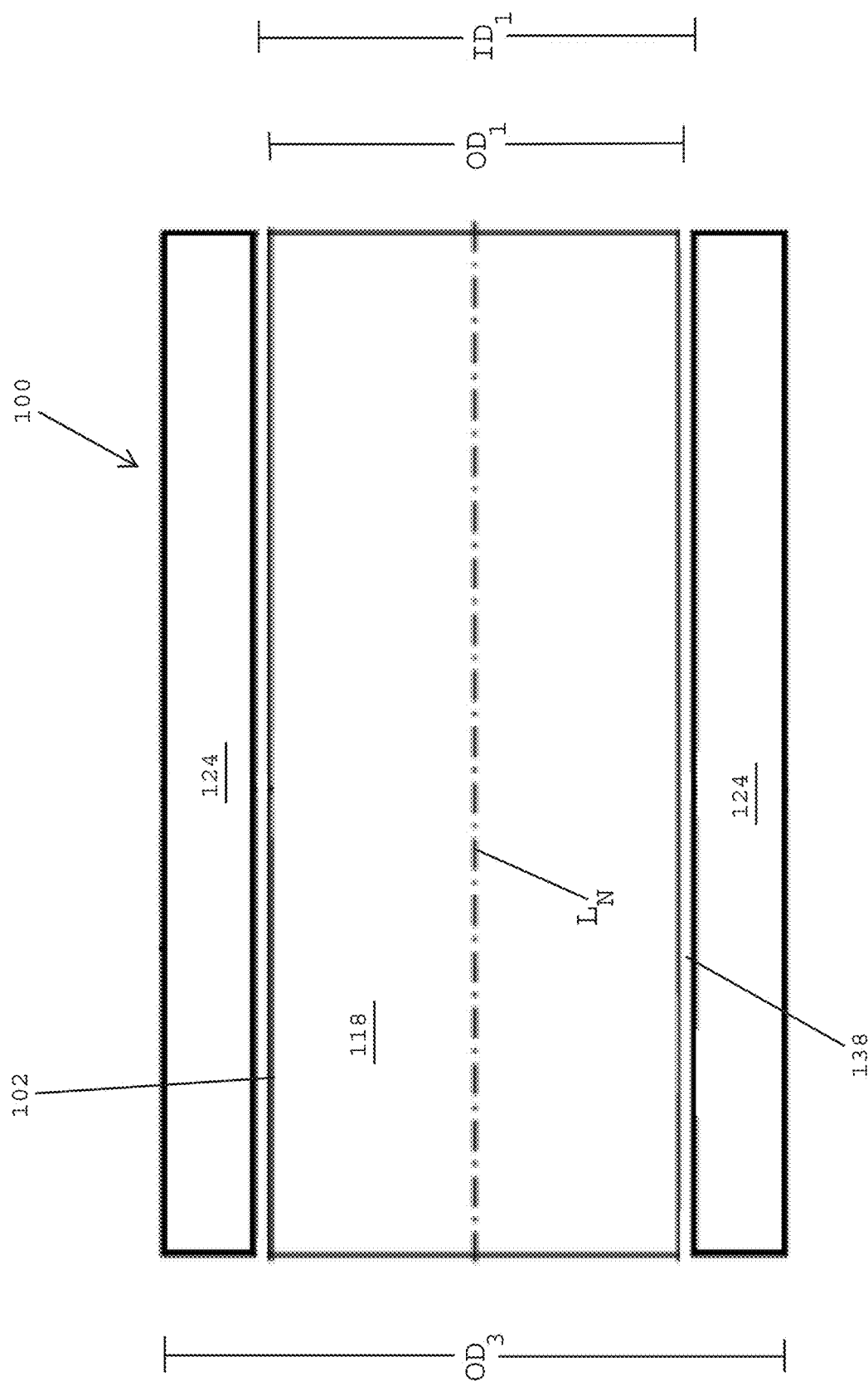
FIG. 4D is still another cross-section view of the composite suture needle shown in FIG. 4A.

Referring to FIGS. 4B-4D, in one embodiment, the sheath 124 may be affixed to the reduced diameter section 118 of the elongated body 102 by applying heat to the sheath to cause the inner diameter $ID_1$ of the sheath to shrink in size so as to hug or snuggly fit the outer surface of the reduced diameter section 118, thereby forming the composite suture needle 100 having a more elastic section. In one embodiment, the more elastic section of the composite suture needle is preferably the section of the composite suture needle where the sheath 124 extends over the reduced diameter section 118.

In one embodiment, the sheath 124 may be affixed to the reduced diameter section 118 of the elongated body 102 by applying an adhesive within a space 138 that is located between an outer surface of the reduced diameter section 118 and an inner surface of the sheath 124.

In one embodiment, the sheath 124 may be affixed to the reduced diameter section 118 of the elongated body 102 by using a linking material disposed within the space 138 that is located between the outer surface of the reduced diameter section 118 and the inner surface of the sheath 124, whereby the linking material is preferably weldable to both the material used to make the elongated body 102 (e.g., stainless steel) and the material used to make the sheath 124 (e.g., nitinol).

In one embodiment, the composite suture needle 100 preferably includes the reduced diameter section 118 and the sheath 124 that overlies the reduced diameter section. The length of the elongated body 118 that is covered by the sheath 124 preferably defines a more elastic region of composite suture needle 100, which is designed to flex (e.g., flatten) when being passed through a smaller cannula without being plastically deformed. Due to the presence of the more elastic region formed by the combination of the reduced diameter section 118 and the highly elastic sheath 124, after the composite suture needle 100 is removed from an end of the cannula (e.g., at a surgical site), the elongated body 102 of the composite suture needle 100 will preferably return (e.g., spring back) to its normal, semi-circular shaped configuration so that the composite suture needle 100 may be used for suturing tissue.

In one embodiment, the composite suture needle disclosed herein is designed to exhibit elasticity for passing through a smaller cannula (e.g., a 5 mm cannula) without substantial plastic deformation. In one embodiment, the elongated body of the composite suture needle (i.e., the elongated body 102 shown in FIG. 2A) is made of stainless steel such as high strength stainless steel. In one embodiment, knowing the yield strength and the Young's modulus for the stainless steel used to make the elongated body of the composite suture needle, the elongated body may be designed with the reduced diameter section having diameter dimensions that will make the composite suture needle elastically deformable without being plastically deformed.

The yield point for a material is the point on a stress-strain curve that indicates the limit of elastic behavior for the material and the beginning of plastic behavior. Yield strength or yield stress is the material property defined as the stress at which a material begins to deform plastically whereas yield point is the point where nonlinear (elastic+plastic) deformation begins. Prior to the yield point the material will deform elastically and will return to its original shape when the applied stress is removed. Once the yield point is passed, however, some fraction of the deformation will be permanent and non-reversible. The yield point determines the limits of performance for mechanical components, since it represents the upper limit to forces that can be applied without permanent deformation.

The Young's modulus of a material is one way to measure the modulus of elasticity of a material. A modulus of elasticity is a quantity that measures an object's resistance to being deformed elastically (i.e., non-permanently) when a stress is applied to it. The modulus of elasticity of an object is defined as the slope of its stress-strain curve in the elastic deformation region. A stiffer material will have a higher modulus of elasticity.

Specifying how stress and strain are to be measured, including directions, allows for many types of elastic moduli to be defined. Young's modulus (E) describes tensile elasticity, or the tendency of an object to deform along an axis when opposing forces are applied along that axis. It is defined as the ratio of tensile stress to tensile strain. It is often referred to simply as the elastic modulus.

In one embodiment, the elongated body of the composite suture needle is preferably elastically deformable from a half-circle shape to a flatter shape having a straightened section without plastically deforming the elongated body of the composite suture needle. As a result, when the elastic suture needle is passed through a smaller cannula and is extracted at a surgical site, the elongated body of the composite suture needle will preferably spring back to its original half circle shape.

As is known to those skilled in the art, most materials can withstand a modest degree of strain before becoming plastically deformed. In one embodiment, the sheath 124 is preferably made of a highly elastic material (e.g., nitinol) that will withstand more strain, as compared to less elastic materials (e.g., stainless steel) before becoming plastically deformed. In one embodiment, the composite suture needle 100 includes a highly elastic material at the greatest distances from the neutral axis $L_N$ (FIG. 4D), which will be able to withstand more flexing before becoming plastically deformed as compared to a conventional suture needle made from a single, less elastic material (e.g., stainless steel) having uniform elastic properties. This is because the outer diameter $OD_1$ of the reduced diameter section 118 of the elongated body 102 is smaller than the outer diameter $OD_3$ of the composite suture needle 100.

Figure 5A:
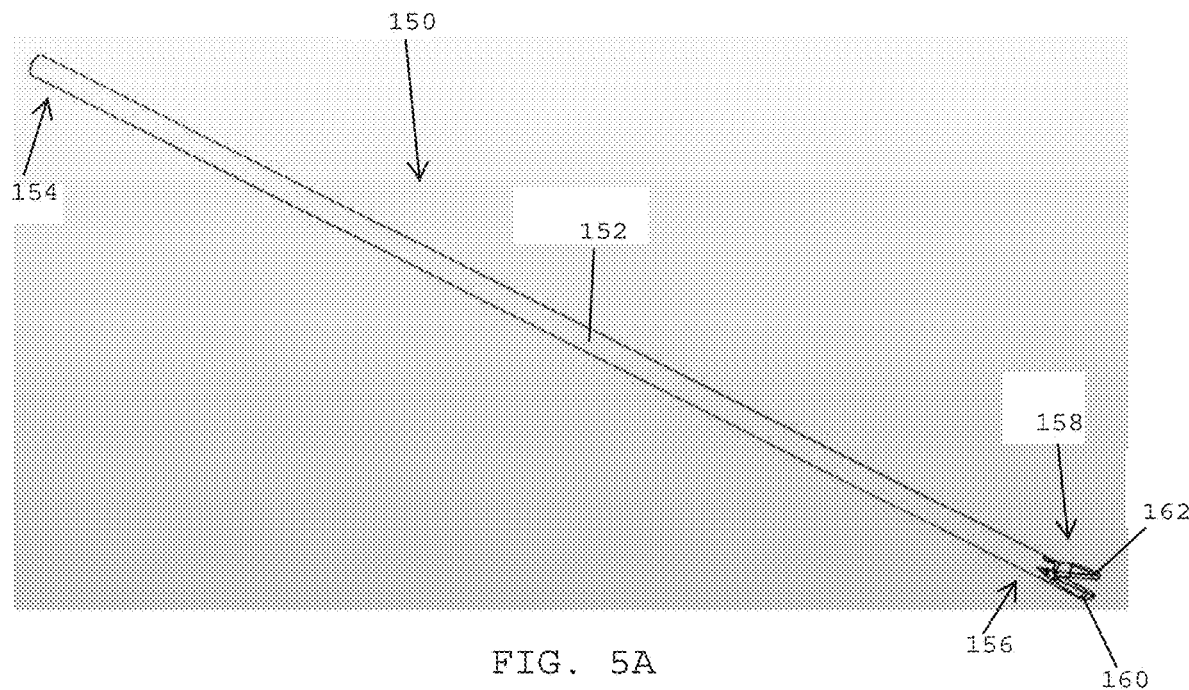
FIG. 5A is a perspective view of a distal section of a needle driver having a clamping assembly at a distal end thereof, in accordance with one embodiment of the present patent application.
Figure 5B:
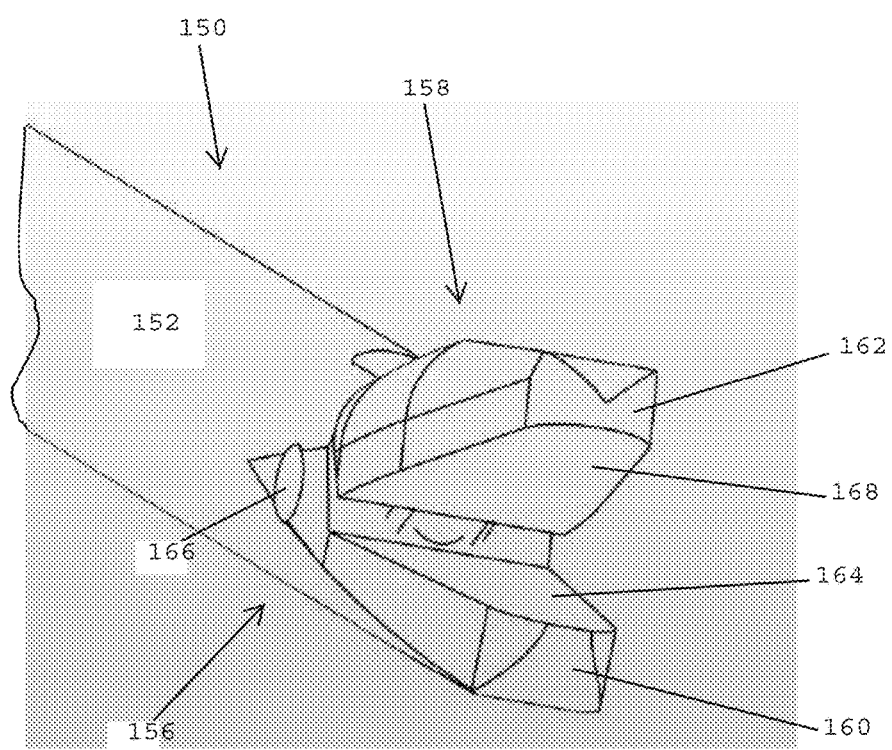
FIG. 5B is a perspective view of the clamping assembly located at a distal end of the needle driver shown in FIG. 5A.

Referring to FIGS. 5A and 5B, in one embodiment, a clamping element such as a needle driver 150 may be utilized for securing a composite suture needle, such as the composite suture needle 100 shown and described above in FIGS. 2A-2B, 3A-3B, and 4A-4D, to remove the composite suture needle from a suture needle package and/or to advance the composite suture needle through the lumen of a cannula to position the composite suture needle at a surgical site for performing a suturing operation. In one embodiment, the shape of the elongated body of the composite suture needle may change (e.g., flatten) as the needle driver 150 advances the composite suture needle through the cannula. In one embodiment, the composite suture needle may have a semi-circular shape that defines a first height $H_1$ (FIG. 4A) and a more elastic midsection that enables the composite suture needle to flex from the half circle shape to a flatter shape. As the needle driver 150 advances the composite suture needle through a cannula having an inner diameter that is smaller than the first height $H_1$ of the composite suture needle 100 (FIG. 4A), the inner walls of the cannula may apply external forces upon the elongated body of the composite suture needle whereupon the elongated body of the composite suture needle will flatten out or become straighter along the reduced diameter section 118 (FIG. 4B) of the elongated body of the composite suture needle for transforming to a smaller, second height for fitting through the smaller inner diameter of the cannula. Upon being extracted from the end of the cannula, the inner walls of the cannula no longer apply the external forces upon the composite suture needle, whereupon the elongated body of the composite suture needle will preferably transform back (e.g., spring back) to its original half circle shape having the first height $H_1$ (FIG. 4A).

In one embodiment, the needle driver 150 preferably includes an elongated shaft 152 having a proximal end 154 and a distal end 156 with a clamping assembly 158 that is movable between open and closed positions. In one embodiment, the clamping assembly 158 preferably includes a lower jaw 160 and an opposing upper jaw 162 that is movable between open and closed positions. In one embodiment, with the clamping assembly 158 in the open position, the lower and upper jaws 160, 162 may be guided into alignment with the tip 116 of the composite suture needle 100 (FIG. 2A). In one embodiment, after the lower and upper jaws are aligned with the tip of the composite suture needle, the jaws may be moved to the closed position for clamping and/or gripping the tapered section 108 (FIG. 2A) of the elongated body 102 of the composite suture needle with the tip 116 preferably positioned between and surrounded by the opposing lower and upper jaws.

Referring to FIG. 5B, in one embodiment, the lower jaw 160 may be stationary, rigidly secured, and/or integral to the distal end 156 of the elongated shaft 152 of the needle driver 150 so that the lower jaw 160 is fixed and does not move relative to the distal end 158 of the elongated shaft 152 of the needle driver 150. In one embodiment, the lower jaw 160 preferably includes a substantially flat top surface 164 that is adapted to be aligned with the tip 116 (FIG. 2A) of the composite suture needle. In one embodiment, the substantially flat top surface 164 of the lower jaw 160 may include a surface roughening such as knurling for enhancing gripping of the distal end of the composite suture needle when the clamping assembly 158 is in the closed position.

In one embodiment, the upper jaw 162 of the clamping assembly 158 is desirably pivotally secured to the distal end 156 of the elongated shaft 152 of the needle driver 150 via a pivot 166, which pivotally secures a proximal end of the upper jaw 162 to the distal end 156 of the elongated shaft 152. The upper jaw 162 preferably includes a substantially flat bottom surface 168 that opposes the substantially flat top surface 164 of the lower jaw 160. The substantially flat bottom surface 168 of the upper jaw 162 may include a surface roughening such as knurling for gripping the distal end of the composite suture needle when the clamping assembly 158 is in the closed position.

Referring to FIGS. 5A and 5B, in one embodiment, when the lower and upper jaws 160, 162 are in the closed position for clamping, gripping and/or securing the tapered section 108 of the elongated body 102 of the composite suture needle 100, the top surface 164 of the lower jaw 160 engages a surface of the tapered section 108 at the distal end 106 of the elongated body 102 composite suture needle 100, and the bottom surface 168 of the upper jaw 162 preferably engages another surface of the tapered section 108 of the elongated body 102 at the distal end 106 of the composite suture needle 100, with the tip 116 of the composite suture needle being located between the opposing jaws. In one embodiment, when the jaws are closed, the top and bottom surfaces 164, 168 of the respective lower and upper jaws 160, 162 may be spaced away from the tip 116 so that the tip is not marred, bent, damaged, or dulled by the jaws of the clamping assembly. In one embodiment, the closed jaws 160, 162 preferably surround the outer perimeter of the tip 116 as the composite suture needle 100 is passed through a cannula for preventing the tip from scratching or being damaged by an inner wall of a cannula.

In one embodiment, a suture needle package may hold one or more composite suture needles, such as the composite suture needle 100 shown in FIGS. 4A-4D, so that the tip 116 of the suture needle 100 is pre-positioned at a location that will facilitate aligning the tip 116 between the top and bottom surfaces 164, 168 of the respective lower and upper jaws 160, 162 of the clamping assembly 158 of the needle driver 150.

Figure 6A:
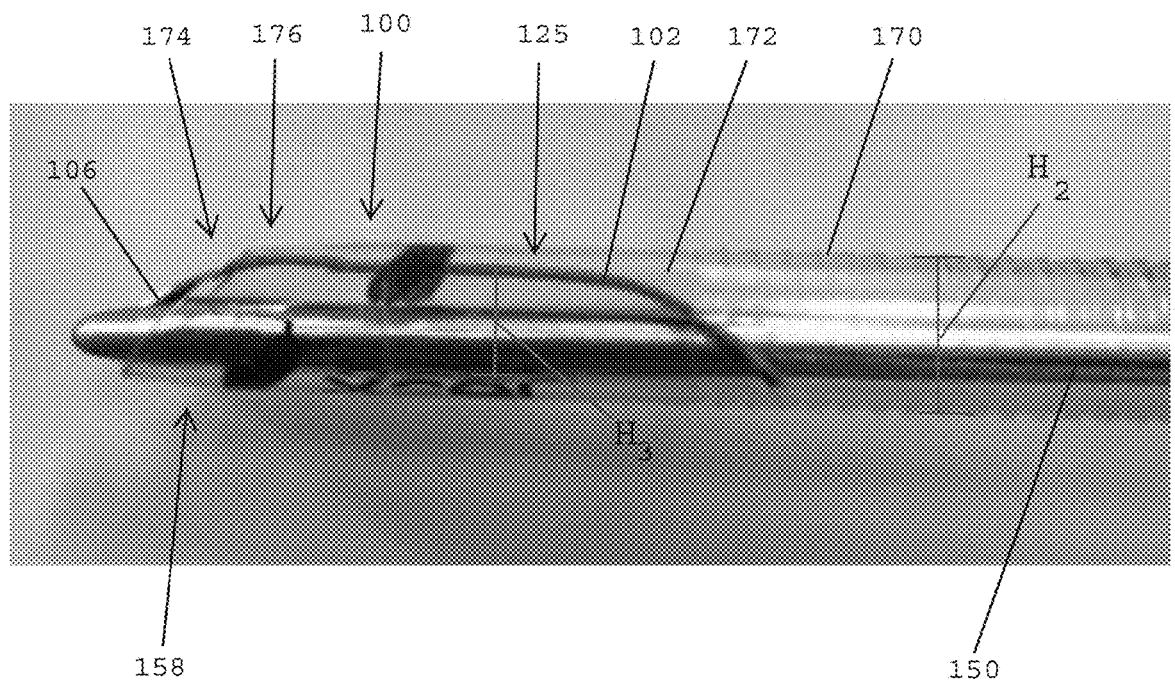
FIG. 6A shows a stage of a method of using a needle driver to advance a composite suture needle having a highly elastic section toward a distal end of a cannula, in accordance with one embodiment of the present patent application.

Referring to FIG. 6A, in one embodiment, after the clamping assembly 158 of the needle driver 150 has been closed for clamping onto the distal end 106 of the elongated body 102 of the composite suture needle 100, the needle driver 150 may be utilized for advancing the suture needle 100 through a cannula 170 to position the suture needle at a surgical site for performing a suturing operation. In one embodiment, the cannula 170 preferably has an elongated conduit 172 having an inner diameter that defines a second height $H_2$ that is less than the first height $H_1$ (FIG. 4A) of the composite suture needle. The elongated conduit 172 preferably extends to an opening 174 at a distal end 176 of the cannula 170. The clamping assembly 158 of the needle driver 150, clamped onto the distal end 106 of the elongated body 102 of the composite suture needle 100, may be advanced toward the distal end of the conduit 172 of the cannula 170 for pulling the composite suture needle 100 through the cannula. As the composite suture needle 100 is pulled by the clamping assembly 158 of the needle driver 150 toward the distal end 176 of the cannula 170, the composite suture needle 100 is required to fit through the smaller conduit 172 having the second height $H_2$ that is less than the original, first height $H_1$ (FIG. 4A) of the composite suture needle 100. Because the composite suture needle 100 is capable of elastically deforming at a midsection 125, the elongated body 102 of the composite suture needle 100 preferably elastically deforms (e.g., straightens out, becomes flatter) as shown in FIG. 6A.

In FIG. 6A, the more elastic midsection 125 of the composite suture needle 100, which includes the highly elastic sheath 124 (FIGS. 4A-4D) of the composite suture needle 100 preferably straightens or flattens for reducing the overall height of the composite suture needle to a third height $H_3$ that is less than the second height $H_2$ of the conduit 172 of the cannula 170. At the smaller third height $H_3$, the flattened suture needle 100 may be passed through the smaller lumen 172 of the cannula 170. As will be described in more detail herein, the composite suture needle is designed to be substantially elastically deformed as it passes through the smaller cannula, changing from the first height $H_1$ (FIG. 4A) to the third height $H_3$.

Figure 6B:
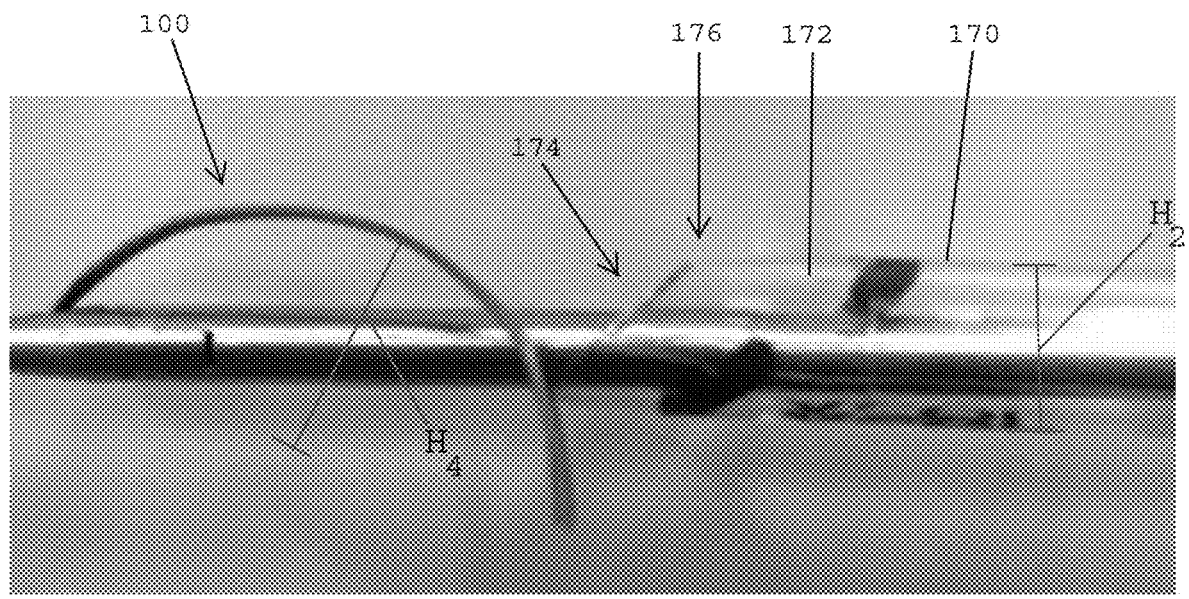
FIG. 6B shows the needle driver and the composite suture needle of FIG. 6A after the composite suture needle has been advanced beyond the distal end of the cannula for being located at a surgical site, in accordance with one embodiment of the present patent application.

Referring to FIG. 6B, after the composite suture needle 100 has been removed from the opening 174 at the distal end 176 of the cannula 170, the composite suture needle 100 will preferably spring back to the original curved configuration (e.g., a half circle shape) having the fourth height $H_4$ that is greater than the second height $H_2$ (FIG. 6A) of the conduit 172 of the cannula 170. Surgical personnel may utilize the composite suture needle 100, in the half circle shape shown in FIG. 6B, for performing a suturing operation at the surgical site.

In one embodiment, after being removed from the distal end 174 of the cannula 170, the composite suture needle 100 preferably springs back to the fourth height $H_4$ that substantially matches the original, first height $H_1$ (FIG. 4A) of the composite suture needle. In one embodiment, the fourth height $H_4$ is about 90% of the original, first height $H_1$. In one embodiment, the fourth height $H_4$ is about 95% of the original, first height $H_1$. In one embodiment, the fourth height $H_1$ substantially matches the original, first height $H_1$.

Figure 6C:
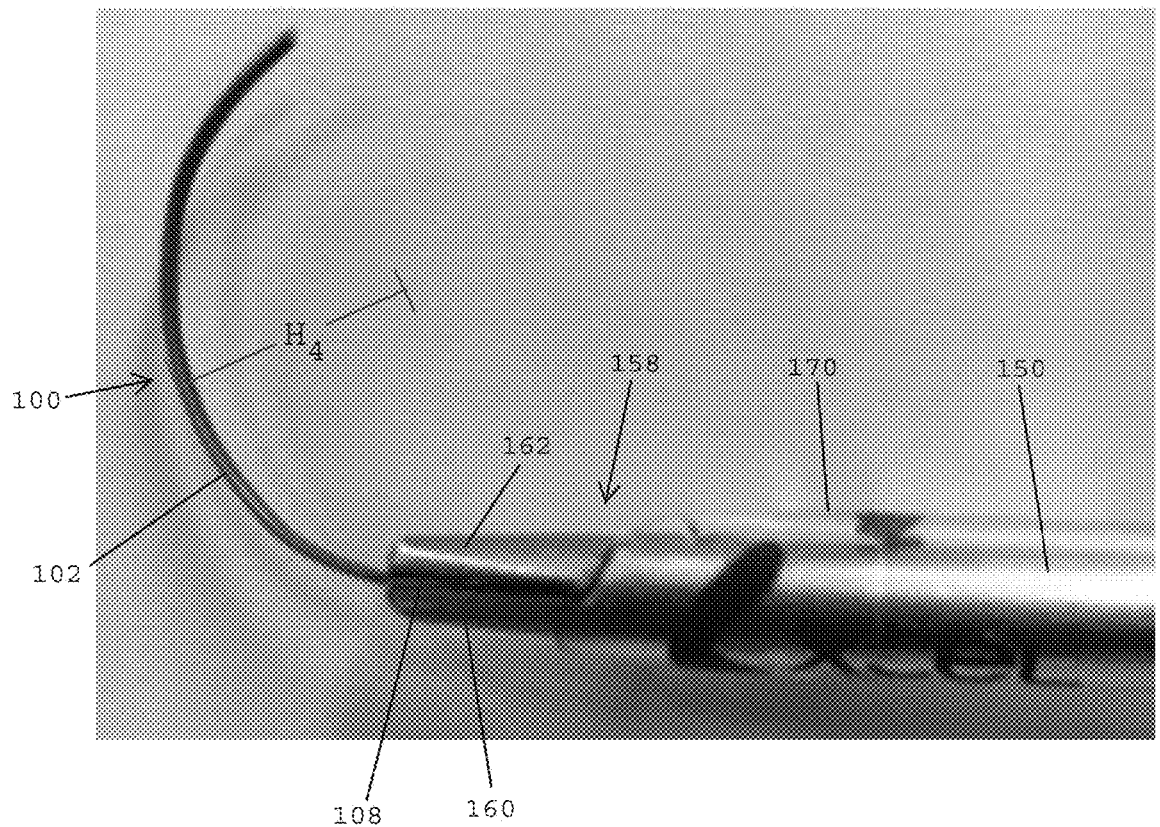
FIG. 6C shows a stage of a method of using a needle driver to retract a composite suture needle from a surgical site and toward a proximal end of the cannula, in accordance with one embodiment of the present patent application.

Referring to FIG. 6C, in one embodiment, at the conclusion of a suturing operation, the curved composite suture needle 100 having the fourth height $H_4$ may be removed from a patient by retracting the composite suture needle through the cannula 170. In one embodiment, the clamping assembly 158 of the needle driver 150 is again closed for securing the tapered section 108 of the elongated body 102 of the curved composite suture needle 100 between the lower jaw 160 and the upper jaw 162 of the needle driver 150.

Figure 6D:
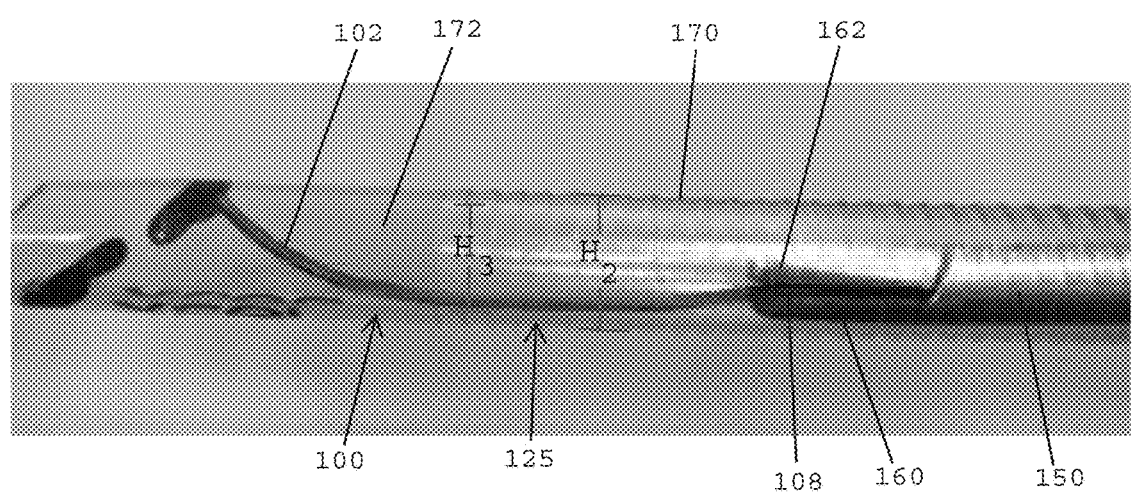
FIG. 6D shows a later stage of a method of retracting the composite suture needle toward the proximal end of the cannula, in accordance with one embodiment of the present patent application.

Referring to FIG. 6D, in one embodiment, at the completion of a suturing operation, the needle driver 150 preferably retracts the composite suture needle 100 through the conduit 172 of the cannula 170. Because the second height $H_2$ of the conduit of the cannula is smaller than the fourth height $H_4$ (FIG. 6B) of the composite suture needle 100, the midsection 125 of the composite suture needle 100 preferably straightens or flattens out to the third height $H_3$ so that the suture needle may be extracted through the conduit 172 of the cannula 170. As the composite suture needle 100 is withdrawn through the cannula 170, the lower and upper jaws 160, 162 of the needle driver 150 preferably engage the tapered section 108 of the elongated body 102 of the composite suture needle 100 and surround the tip 116 (FIG. 4A) of the suture needle to protect the tip from being damaged as the needle is pulled and/or retracted through the cannula 170.

Referring to FIGS. 7A-7C, in one embodiment, a composite suture needle 200 preferably includes an elongated body 202 (i.e., the core component) having a proximal end 204 and a distal end 206. In one embodiment, the distal end 206 of the elongated body 202 preferably includes a tapered section 208 having a proximal end 210 that defines a distal shoulder 212 and a distal end 214 that includes a sharpened or pointed tip 216. The tapered section 208 preferably tapers inwardly between the proximal end 210 and the distal end 214 thereof. In one embodiment, the pointed tip 216 at the distal end 214 of the tapered section 208 preferably defines a leading end of the elongated body 202, which is designed for piercing tissue to facilitate passing the distal end 206 of the elongated body 202 through tissue during a suturing operation.

In one embodiment, the proximal end 204 of the elongated body includes a larger diameter section having a proximal end 205 adapted to have a suture attached hole 207 formed therein and a distal end 209 that defines a shoulder 211.

In one embodiment, the elongated body 202 of the composite suture needle 200 preferably includes a reduced diameter section 218 that extends between the shoulder 211 at the proximal end 204 of the elongated body and the shoulder 212 at the distal end of the elongated body. In one embodiment, the reduced diameter section 218 has a cross-section having a circular shape, which is configured to receive a sheath made of a highly elastic material, as will be described in more detail herein.

In one embodiment, the reduced diameter section 218 of the elongated body 202 preferably defines an outer diameter $OD_4$, the shoulder 211 at the proximal end of the elongated body defines an outer diameter $OD_5$, and the shoulder 212 at the distal end of the elongated body also defines an outer diameter $OD_5$, whereby the outer diameters $OD_5$ of the respective shoulders 211, 212 are greater than the outer diameter $OD_4$ of the reduced diameter section 218 of the elongated body 202 that extends between the shoulders.

In one embodiment, the elongated body 202 may be curved and/or may have a half circle or semi-circular shape. In one embodiment, the reduced diameter section 218 of the elongated body 202 is curved and preferably includes a concave surface 220 that extends along the inside of the curve of the reduced diameter section and a convexly curved outer surface 222 that extends along the outside of the curve of the reduced diameter section 218.

In one embodiment, the elongated body 202 may be made of strong alloys such as stainless steels. In one embodiment, the stainless steels may include austenitic stainless steels (302SS), and martensitic-aged (mar-aged) stainless steels (455SS).

Figure 8A:
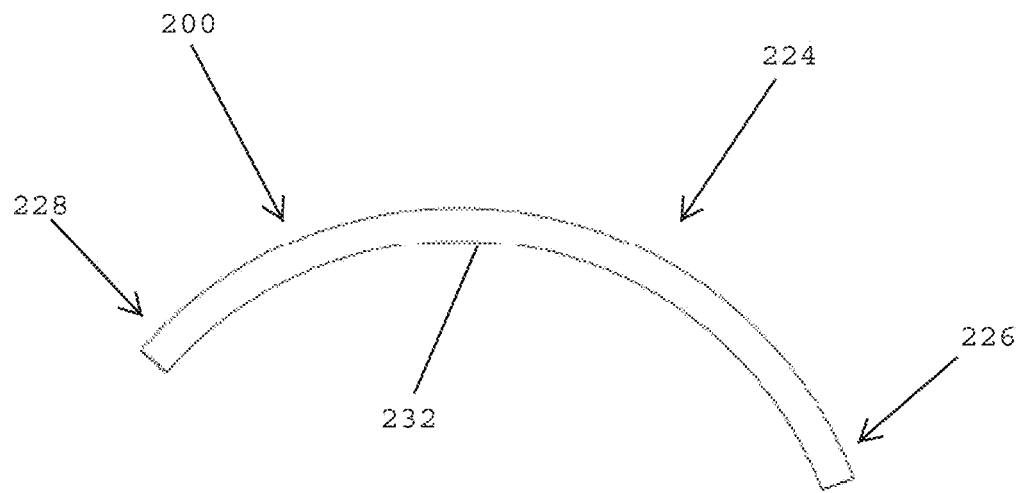
FIG. 8A is a side view of a sheath of a composite suture needle, in accordance with one embodiment of the present patent application.
Figure 8B:
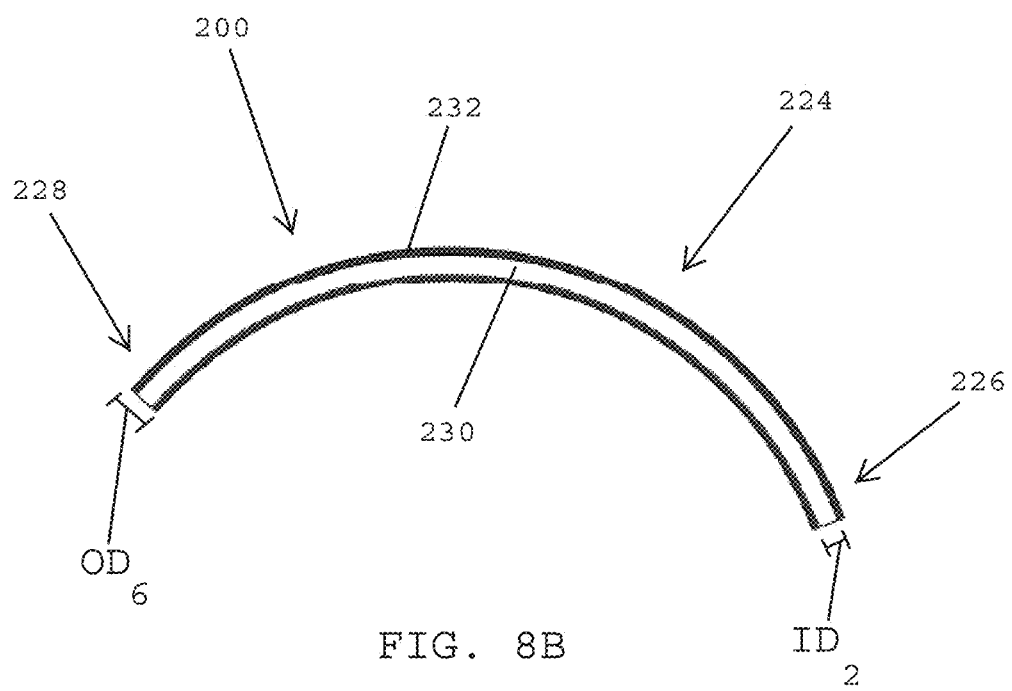
FIG. 8B is a cross-sectional view of the sheath shown in FIG. 8A.

Referring to FIGS. 8A and 8B, in one embodiment, the composite suture needle 200 preferably includes a sheath 224 made of a material having higher level of elasticity than the material used to make the elongated body 202 (FIGS. 7A-7C). In one embodiment, the sheath 224 may be made of a highly elastic material such as nitinol. In one embodiment, the sheath 224 may have a sleeve, tubular, or cylindrical shape. In one embodiment, the sheath 224 is preferably sized, shaped and/or configured to be assembled over the reduced diameter section 218 of the elongated body 102 (FIGS. 7A-7C) to form the composite suture needle 200 including the elongated body, which is relatively less elastic, and the sheath 224, which is relatively more elastic than the material used to make the elongated body.

In one embodiment, the sheath 224 preferably has a proximal end 226, a distal end 228, and a lumen 230 that extends from the proximal end 232 to the distal end 234 thereof. Referring to FIGS. 7A-7C and 8B, in one embodiment, the lumen 236 of the sheath 224 desirably defines an inner diameter $ID_2$ that is slightly larger than the outer diameter $OD_4$ of the reduced diameter section 218 of the elongated body 202. In one embodiment, the sheath 224 has an outer surface 232 that preferably defines an outer diameter $OD_6$ that approximates the outer diameters $OD_5$ of the respective shoulders 211, 212 of the elongated body 202. In one embodiment, when the sheath 224 is assembled over the reduced diameter section 218 of the elongated body to form a composite suture needle 200, the distal end 228 of the sheath 224 preferably abuts against the shoulder 212 at the distal end of the elongated body and the proximal end 226 of the sheath 224 preferably abuts against the shoulder 211 at the proximal end of the elongated body. In one embodiment, the outer surface 232 at the distal end 228 of the sheath 224 approximates the outer surface at the proximal end 210 of the tapered section 208 to provide a smooth transition between the tapered section 208 and the sheath 224 of the composite suture needle, and the outer surface 232 at the proximal end 226 of the sheath 224 approximates the outer surface at the distal end 209 of the proximal end 204 of the elongated body 202 to provide for a smooth transition between the proximal end of the sheath and larger diameter section at the proximal end of the elongated body.

In one embodiment, when the sheath is assembled with the elongated body to form a composite suture needle, the sheath preferably traverses the majority of the length of the elongated body.

Figure 9A:
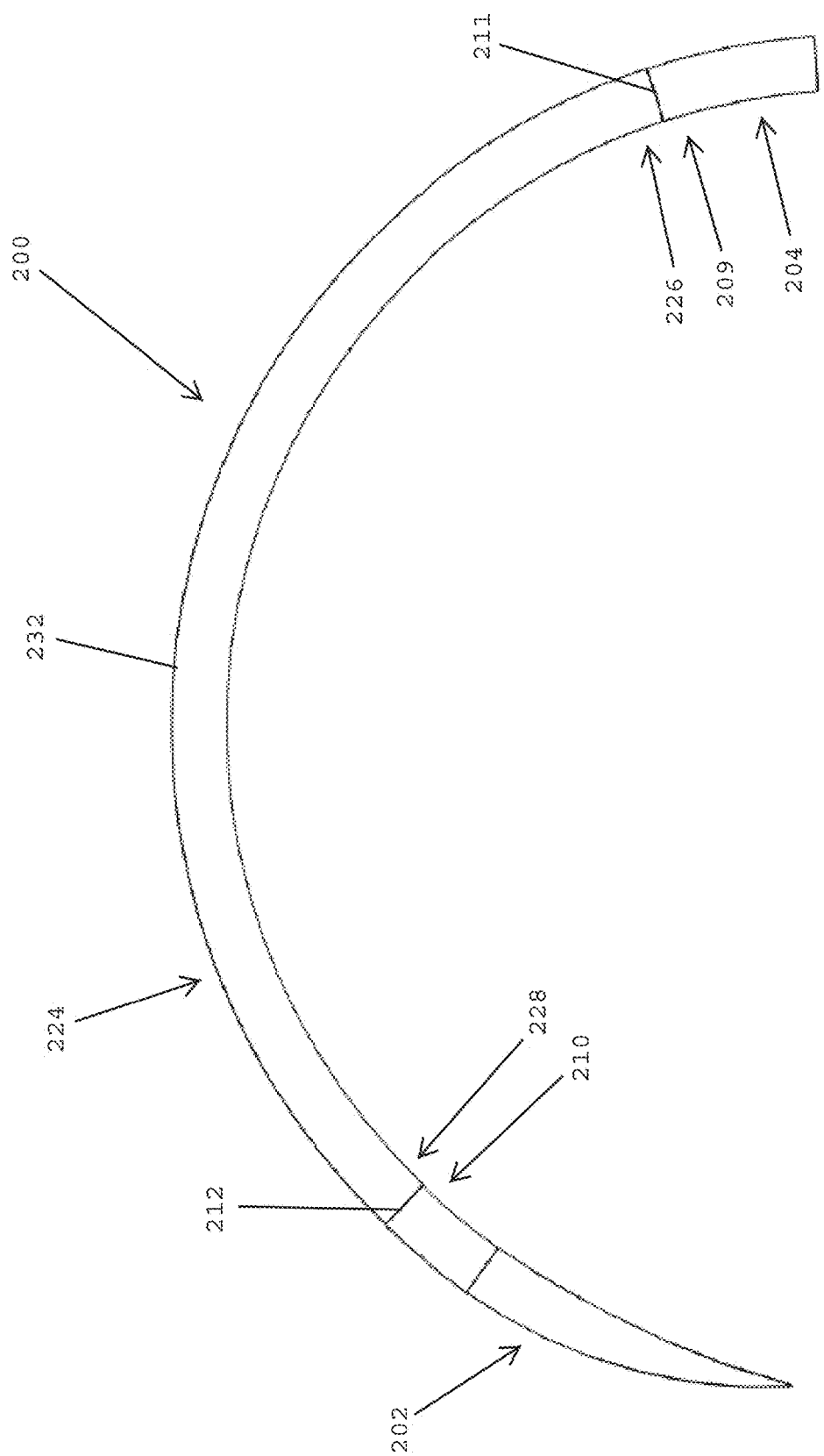
FIG. 9A is a side view of a composite suture needle including the sheath of FIGS. 8A and 8B assembled with the elongated body of FIGS. 7A-7C, in accordance with one embodiment of the present patent application.
Figure 9B:
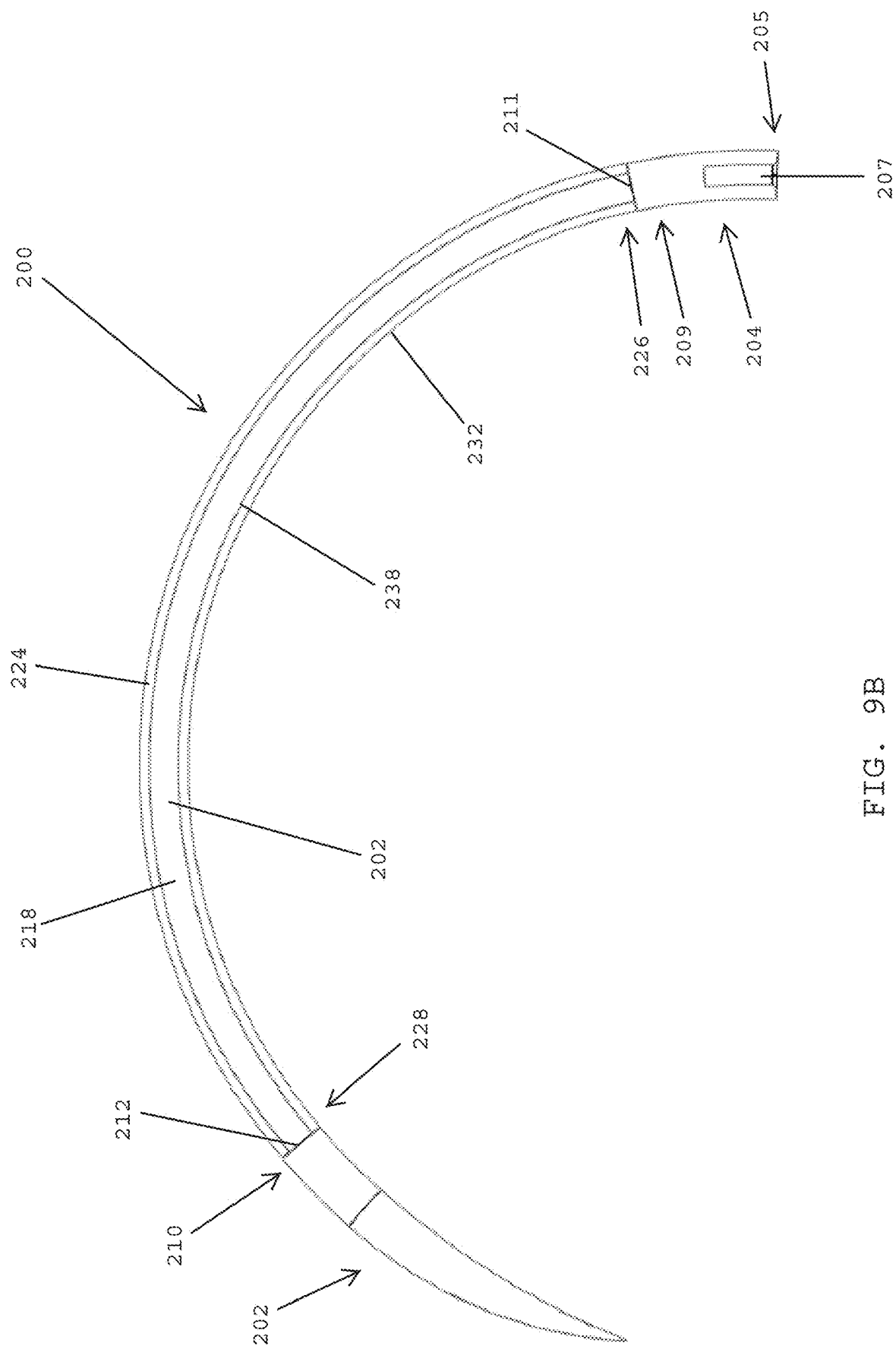
FIG. 9B is a cross-sectional view of the composite suture needle shown in FIG. 9A.

Referring to FIGS. 9A and 9B, in one embodiment, the composite suture needle 200 may be formed by assembling the sheath 224 over the reduced diameter section 218 of the elongated body 202. In one embodiment, the distal end 228 of the sheath 224 preferably abuts against the shoulder 212 (FIG. 8B) at the distal end of the elongated body 202 and the proximal end 226 of the sheath 224 abuts against the shoulder 211 at the proximal end of the elongated body 202.

The inner diameter $ID_2$ (FIG. 8B) of the sheath 224 is preferably slightly larger than the outer diameter $OD_4$ (FIGS. 7B and 7C) of the reduced diameter section 218 of the elongated body 202. The outer surface 232 of the sheath 224 preferably defines an outer diameter $OD_6$ (FIG. 8B) that approximates the outer diameter $OD_5$ (FIG. 7B) at the proximal end 210 of the tapered section 208 of the elongated body 202 and the outer diameter $OD_5$ (FIG. 7C) at the distal end 209 of the proximal end 204 of the elongated body 202.

In one embodiment, after the sheath 224 has been assembled over the reduced diameter section 218 of the elongated body 202, the proximal end 226 of the sheath 224 preferably abuts against the shoulder 211 at the proximal end of the elongated body and the distal end 228 of the sheath 224 preferably abuts against the shoulder 212 at the distal end of the elongated body 202. In one embodiment, the suture receiving hole 207 is formed in the proximal end 204 of the elongated body 202 for attaching an end of a suture thread to the proximal end of the composite suture needle.

Referring to FIG. 9B, in one embodiment, the sheath 224 may be affixed to the reduced diameter section 218 of the elongated body 202 by applying heat to the sheath to cause the inner diameter of the sheath to shrink in size so as to hug or snuggly fit the outer surface of the reduced diameter section 218, thereby forming the composite suture needle 200 having a more elastic section. In one embodiment, the sheath 224 may be affixed to the reduced diameter section 218 of the elongated body 202 by applying an adhesive within a space 238 that is located between an outer surface of the reduced diameter section 218 and an inner surface of the sheath 224.

In one embodiment, the sheath 224 may be affixed to the reduced diameter section 218 of the elongated body 202 by using a linking material disposed within the space 238 that is located between the outer surface of the reduced diameter section 218 and the inner surface of the sheath 224, whereby the linking material is preferably weldable to both the material used to make the elongated body 202 (e.g., stainless steel) and the material used to make the sheath 224 (e.g., nitinol).

In one embodiment, the composite suture needle 200 preferably includes the reduced diameter section 218 and the sheath 224 that overlies the reduced diameter section. The length of the elongated body 202 that is covered by the sheath 224 preferably defines a more elastic region of the composite suture needle 200, which is designed to flex (e.g., flatten) when being passed through a smaller cannula without being plastically deformed. Due to the presence of the more elastic region formed by the combination of the reduced diameter section 218 and the highly elastic sheath 224, after the composite suture needle 200 is removed from an end of the cannula (e.g., at a surgical site), the elongated body 202 of the composite suture needle 200 will preferably return (e.g., spring back) to its normal, semi-circular shaped configuration so that the composite suture needle 200 may be used for suturing tissue.

Figure 10:
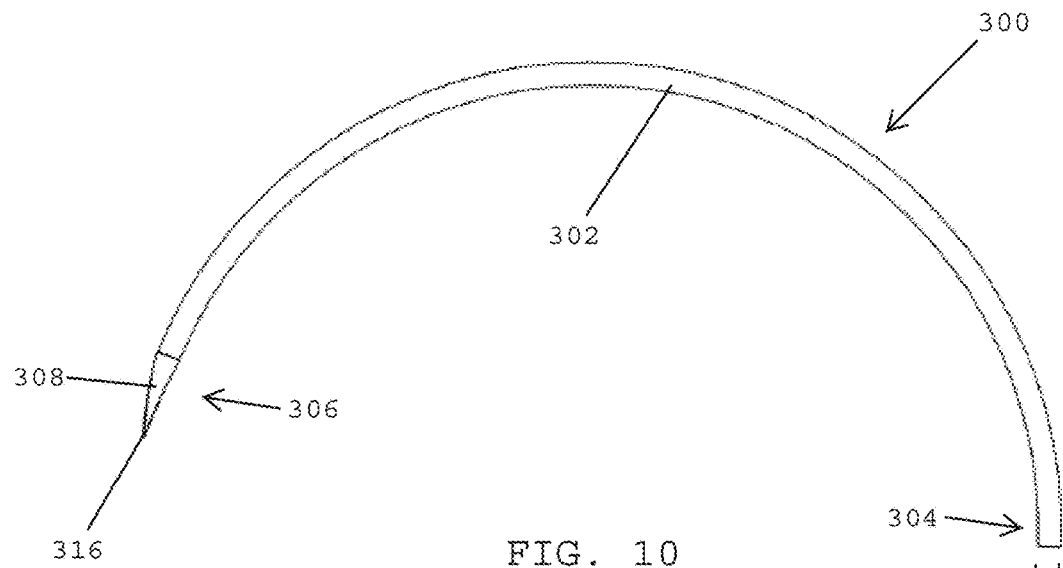
FIG. 10 is a side view of an elongated body of a composite suture needle, in accordance with one embodiment of the present patent application.

Referring to FIG. 10, in one embodiment, a composite suture needle 300 preferably includes an elongated body 302 (i.e., the core component) having a proximal end 304 and a distal end 306 having a tapered section 308 that terminates at a sharpened or pointed tip 316. The tapered section 308 preferably tapers inwardly to the sharpened tip 316. The sharpened tip 316 desirably defines a leading end of the elongated body 302 that is adapted to pierce tissue during a suturing operation.

In one embodiment, the elongated body 302 preferably defines an outer diameter $OD_7$. In one embodiment, the elongated body 302 may be curved and/or may have a half circle or semi-circular shape. In one embodiment, the elongated body 302 is curved and preferably includes a concave surface 320 that extends along the inside of the curve of the elongated body and a convexly curved outer surface 322 that extends along the outside of the curve of the elongated body.

In one embodiment, the elongated body 302 may be made of strong alloys such as stainless steels. In one embodiment, the stainless steels may include austenitic stainless steels (302SS), and martensitic-aged (mar-aged) stainless steels (455SS).

Figure 11A:
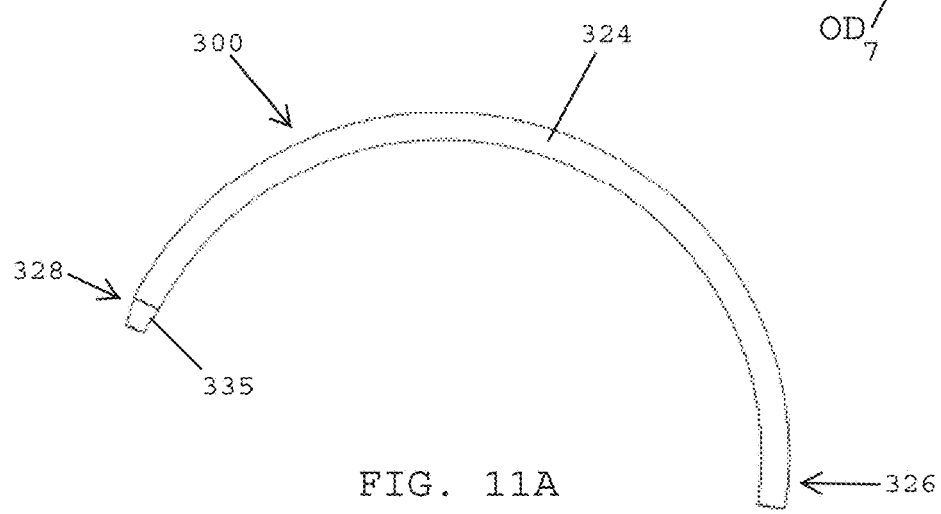
FIG. 11A is a side view of a sheath of a composite suture needle, in accordance with one embodiment of the present patent application.
Figure 11B:
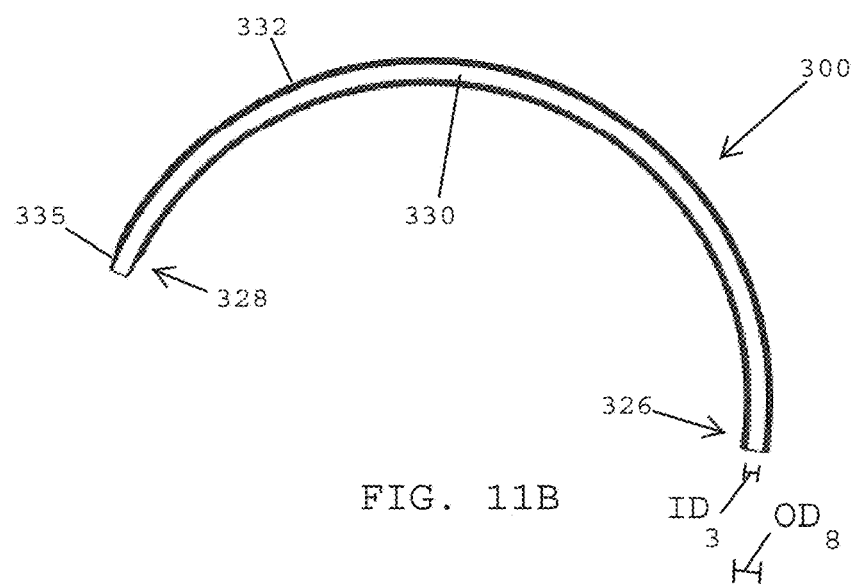
FIG. 11B is a cross-sectional view of the sheath shown in FIG. 11A.

Referring to FIGS. 11A and 11B, in one embodiment, the composite suture needle 300 preferably includes a sheath 324 made of a material having higher level of elasticity than the material used to make the elongated body 302 (FIG. 10) of the composite suture needle. In one embodiment, the sheath 324 may be made of a highly elastic material such as nitinol. In one embodiment, the sheath 324 may have a sleeve, tubular, or cylindrical shape. In one embodiment, the sheath 324 is preferably sized, shaped and/or configured to be assembled over the elongated body 302 (FIG. 10) to form the composite suture needle 300 including the elongated body, which is relatively less elastic, and the sheath 324, which is relatively more elastic than the material used to make the elongated body.

In one embodiment, the sheath 324 preferably has a proximal end 326, a distal end 328 with a tapered outer surface 335, and a lumen 330 that extends from the proximal end 326 to the distal end 328 thereof. Referring to FIGS. 10 and 11A-11B, in one embodiment, the lumen 330 of the sheath 324 desirably defines an inner diameter $ID_3$ that is slightly larger than the outer diameter $OD_7$ (FIG. 10) of the elongated body 302. In one embodiment, when the sheath 324 is assembled over the elongated body 302 to form a composite suture needle 300, the tapered outer surface 335 at the distal end 328 of the sheath 324 preferably approximates with the outer surface of the tapered section 308 at the distal end 306 of the elongated body 302 to provide a smooth transition between the distal end 328 of the sheath 324 and the tapered section 308 of the elongated body 302.

In one embodiment, when the sheath is assembled with the elongated body to form a composite suture needle, the sheath preferably covers the majority of the length of the composite suture needle. In one embodiment, the sheath may be formed around the elongated body and presented to needle making equipment as a pre-made composite wire. The needle making equipment may be used to grind a tip to expose the stainless steel of the elongated body. The proximal end of the elongated body may be drilled, laser drilled, and/or electro-polished to produce a suture receiving hole.

Figure 12A:
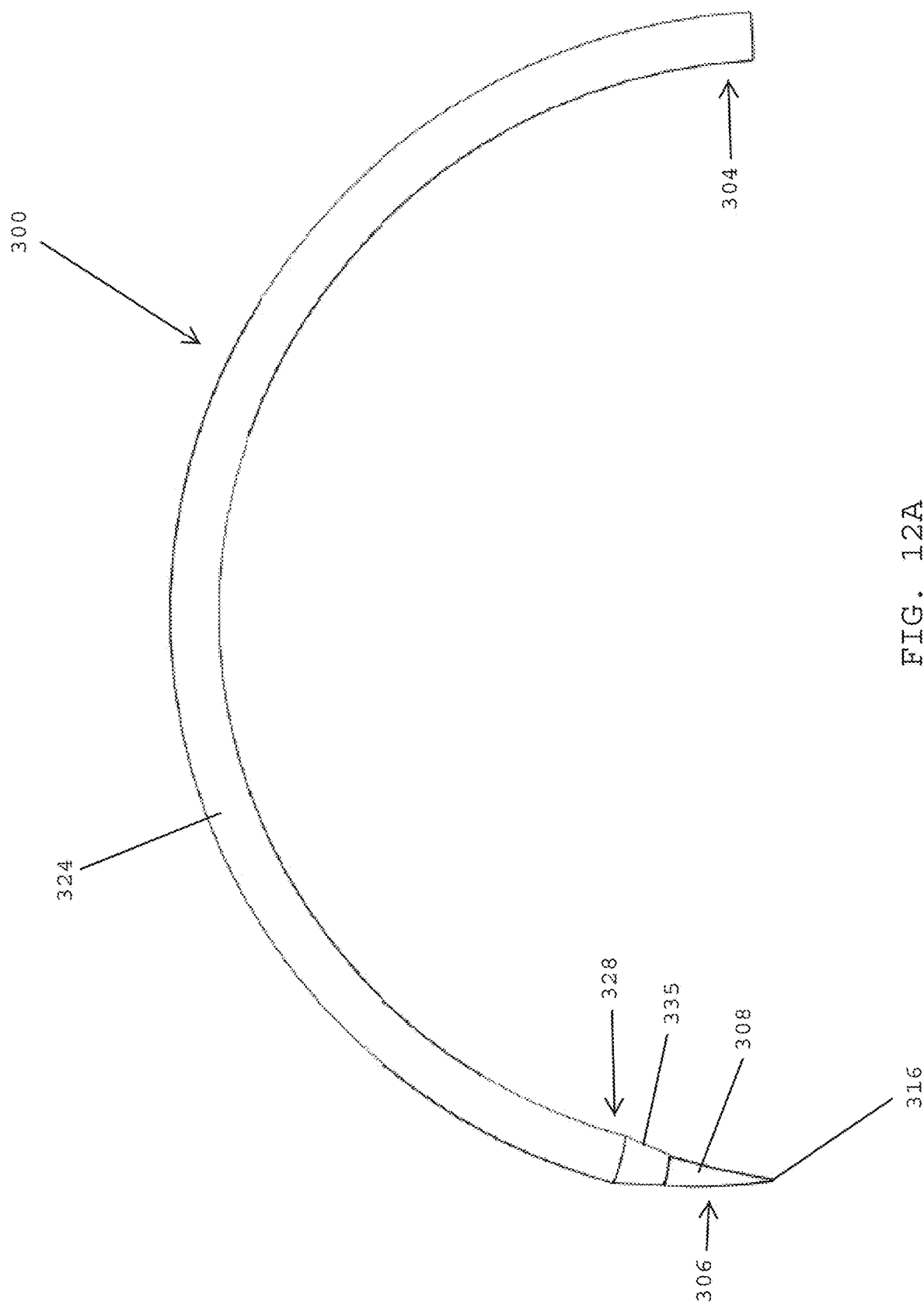
FIG. 12A is a side view of a composite suture needle including the sheath of FIGS. 11A and 11B assembled with the elongated body of FIG. 10, in accordance with one embodiment of the present patent application.
Figure 12B:
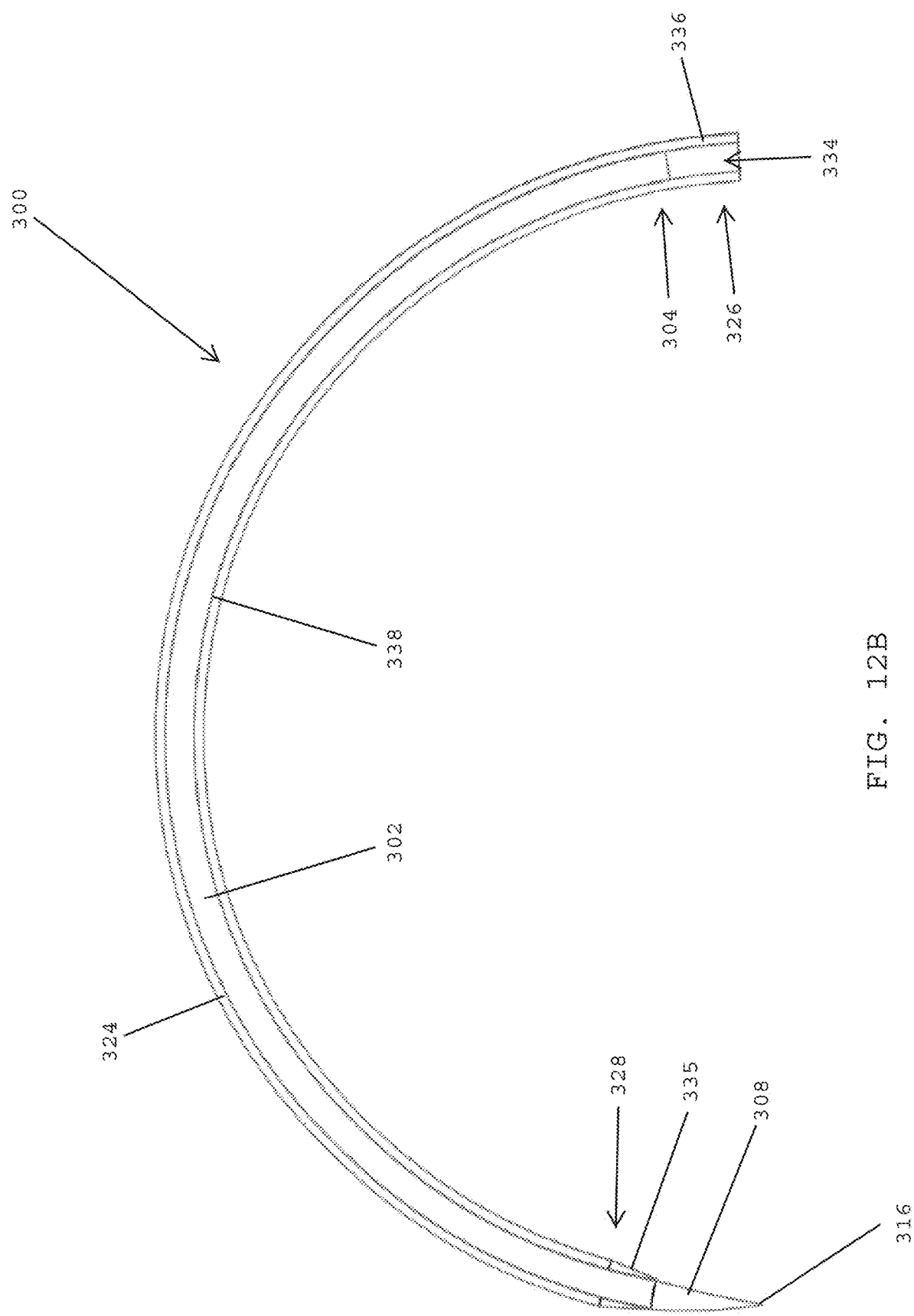
FIG. 12B is a cross-sectional view of the composite suture needle shown in FIG. 12A.

Referring to FIGS. 12A and 12B, in one embodiment, the composite suture needle 300 may be formed by assembling the sheath 324 over the elongated body 302 (FIG. 10). In one embodiment, the tapered section 335 at the distal end 328 of the sheath 324 preferably overlies the tapered section 308 at the distal end 306 of the elongated body 302. The inner diameter $ID_3$ (FIG. 11B) of the sheath 324 is preferably slightly larger than the outer diameter $OD_7$ (FIG. 10) of the elongated body 302.

In one embodiment, after the sheath 324 has been assembled over the elongated body 302, the sharpened tip 316 and a distal portion of the tapered section 308 of the elongated body 302 preferably projects beyond the tapered section 335 at the distal end 328 of the sheath 324.

Referring to FIG. 12B, in one embodiment, the sheath 324 may be affixed to the elongated body 302 by applying heat to the sheath to cause the inner diameter of the sheath to shrink in size so as to hug or snuggly fit the outer surface of the elongated body 302, thereby forming the composite suture needle 300 having an elastic section. In one embodiment, the sheath 324 may be affixed to the elongated body 302 by applying an adhesive within a space 338 that is located between an outer surface of the elongated body 302 and an inner surface of the sheath 324.

In one embodiment, the sheath 324 may be affixed to the elongated body 302 by using a linking material disposed within the space 338 that is located between the outer surface of the elongated body 302 and the inner surface of the sheath 324, whereby the linking material is preferably weldable to both the material used to make the elongated body 302 (e.g., stainless steel) and the material used to make the sheath 324 (e.g., nitinol).

In one embodiment, the composite suture needle 300 preferably includes the elongated body 302 and the sheath 224 that overlies the elongated body. The length of the elongated body 302 that is covered by the sheath 324 preferably defines a more elastic region of composite suture needle 300, which is designed to flex (e.g., flatten) when being passed through a smaller cannula without being plastically deformed. Due to the presence of the more elastic region formed by the combination of the elongated body 302 and the highly elastic sheath 324, after the composite suture needle 300 is removed from an end of the cannula (e.g., at a surgical site), the elongated body 302 of the composite suture needle 300 will preferably return (e.g., spring back) to its normal, semi-circular shaped configuration so that the composite suture needle 300 may be used for suturing tissue.

In one embodiment, after the sheath 324 has been assembled over the elongated body 302, the proximal end 326 of the sheath 324 preferably extends proximally beyond the proximal end 304 of the elongated body 302 to define a suture attachment opening 334 that is located at the proximal end of the composite suture needle 300. The suture attachment opening 334 is preferably surrounded by a swage zone 336 of the sheath 324 that may be swaged or crimped for securing an end of a suture thread to the proximal end of the composite suture needle 300. In one embodiment, an end of a suture thread (not shown) may be inserted into the suture attachment opening 334 of the sheath 324, and the swage zone 336 of the sheath 324 may be swaged for securing the end of the suture thread to the proximal end of the composite suture needle 300.

Figure 13A:
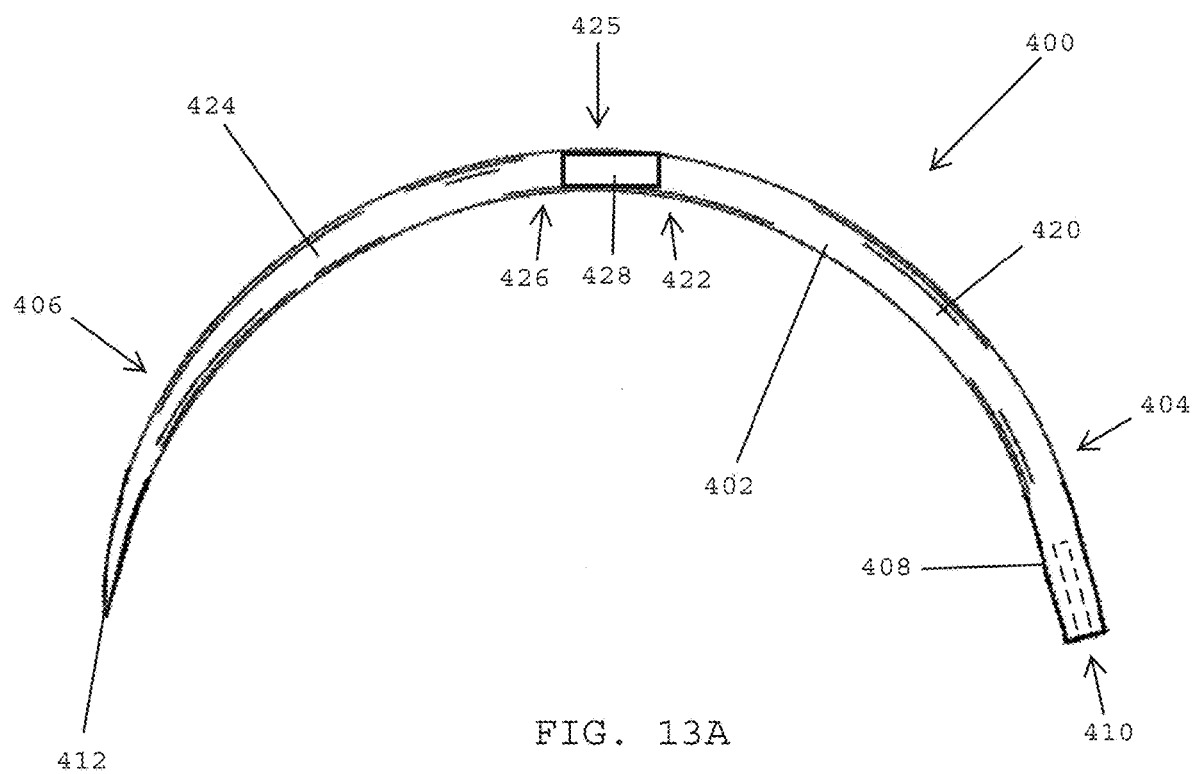
FIG. 13A is a side view of a composite suture needle having an elongated body with a curved configuration and a highly elastic component that interconnects a proximal section and a distal section of the elongated body, in accordance with one embodiment of the present patent application.

Referring to FIG. 13A, in one embodiment, a composite suture needle 400 having a highly elastic midsection 425 preferably includes an elongated body 402 with a proximal end 404 and a distal end 406. The elongated body 402 of the composite suture needle 400 may be curved and may have a half circle or semi-circular shape.

In one embodiment, the highly elastic midsection 425 is configured to be a highly elastic region of the composite suture needle 400 for enabling the composite suture needle to be straightened for being passed through a smaller cannula, and then returned back to its original curved configuration for being used in a suturing operation.

In one embodiment, the composite suture needle 400 desirably includes a suture attachment barrel 408 that is adjacent the proximal end 404 of the elongated body 402, and a suture attachment opening 410 that is formed in a proximal face of the suture attachment barrel 408. An end of a surgical suture (e.g., a filamentary element; a thread) may be inserted into the suture attachment opening 410 and the suture attachment barrel 408 may be swaged for securing the end of the surgical suture to the proximal end 404 of the elongated body 402 of the composite suture needle 400.

In one embodiment, the composite suture needle 400 preferably includes a tip 412, such as a sharpened or pointed tip, that is integral to the distal end 406 of the elongated body 402 and that desirably defines a leading or distal-most end of the composite suture needle 400. The tip 412 is preferably sharpened for piercing tissue to facilitate passing the distal end 406 of the elongated body 402 of the composite suture needle 400 through tissue during a suturing operation.

Figure 13B:
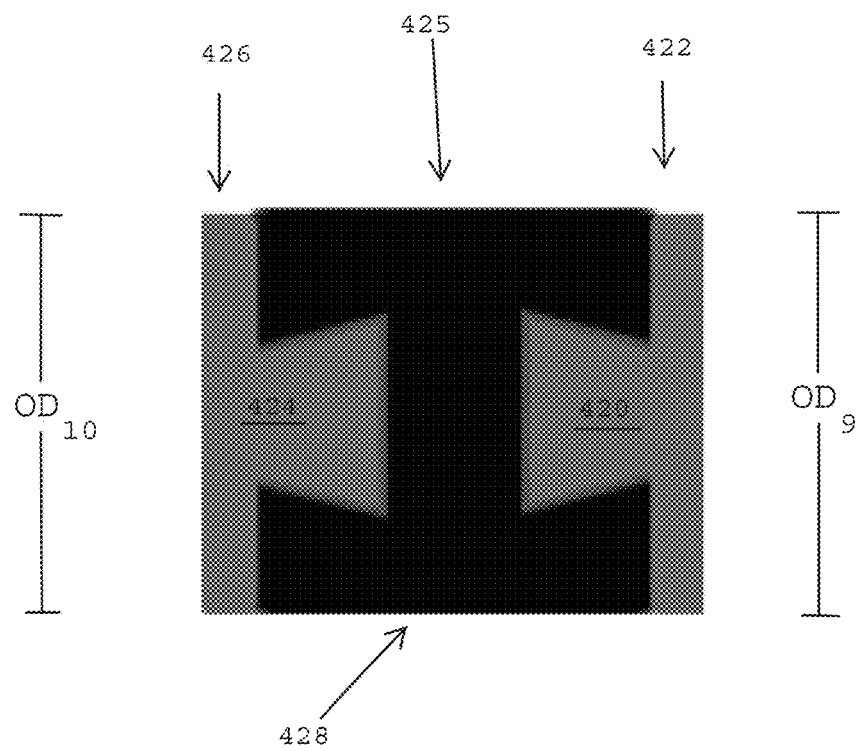
FIG. 13B is a cross-sectional view of the highly elastic component of the composite suture needle shown in FIG. 13A, which interconnects the proximal section and the distal section of the elongated body.

Referring to FIGS. 13A and 13B, in one embodiment, the elongated body 402 preferably has a proximal body section 420 having a distal end 422, a distal body section 424 having a proximal end 426, and a highly elastic connector 428 that interconnects the distal end 422 of the proximal body section 420 and the proximal end 426 of the distal body section 424. The highly elastic connector 428 may include a mechanical connecting structure such as a dovetail-shaped structure for connecting the highly elastic connector with the proximal and distal body sections 420, 424. In one embodiment, the highly elastic connector 428 preferably has an outer diameter $OD_9$ that substantially matches the outer diameters $OD_{10}$ of the respective proximal and distal body sections 420, 424 that bound the ends of the highly elastic connector 428.

In one embodiment, the composite suture needle 400 preferably includes the highly elastic connector 428, which preferably has a higher level of elasticity than the material used to make the proximal and distal body sections 420, 424 of the elongated body 402 of the composite suture needle 400. In one embodiment, the highly elastic connector 428 may be made of a highly elastic material, such as nitinol, and the elongated body 420 including the proximal and distal body sections 420, 424 may be made of stainless steel.

In one embodiment, the highly elastic connector 428 at the midsection 425 of the composite suture needle 400 preferably defines a more elastic region of the elongated body 402, which is designed to flex when being passed through a cannula without being plastically deformed. Due to the presence of the more elastic midsection 425 formed by the highly elastic connector 428, after the composite suture needle 400 is removed from an end of the cannula (e.g., at a surgical site), the elongated body 402 of the composite suture needle 400 will desirably return (e.g., spring back) to its normal, semi-circular shaped configuration so that the composite suture needle 400 may be used for suturing tissue.

Figure 14A:
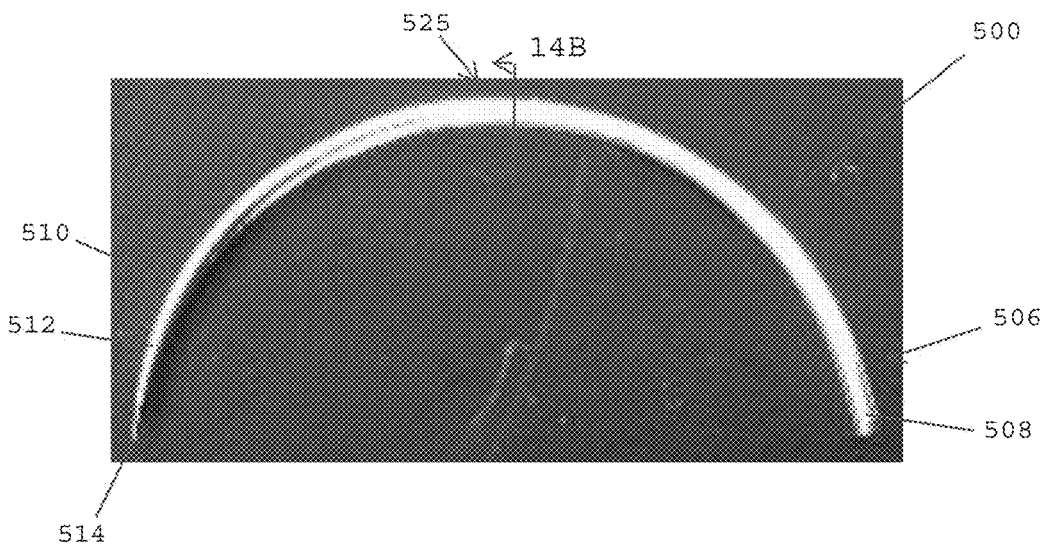
FIG. 14A is a side view of a composite suture needle having a highly elastic section located between proximal and distal ends of the composite suture needle, in accordance with one embodiment of the present patent application.

Referring to FIG. 14A, in one embodiment, a composite suture needle 500 may have a structure that is similar to that shown in described above in the embodiments of FIGS. 4A-4D, 9A-9D, and/or 12A-12B. In one embodiment, the composite suture needle 500 preferably includes an elongated body that extends from a proximal end 506 having a suture attachment barrel 508 that defines a proximal-most end of the composite suture needle and a distal end 510 having a tapered region 512 with a sharpened tip 514 that defines a distal-most end of the composite suture needle 500. In one embodiment, the suture needle 500 preferably includes a bendable or highly elastic region 525 that preferably extends along a majority of the length of the elongated body.

Figure 14B:
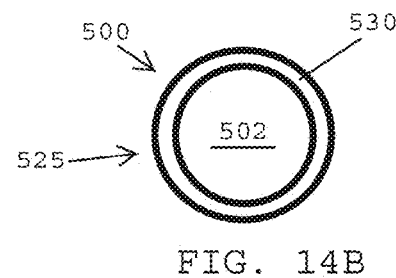
FIG. 14B is a cross-sectional view of the composite suture needle shown in FIG. 14A.

Referring to FIG. 14B, in the embodiment, the highly elastic region 525 of the composite suture needle 500 preferably includes the elongated body 502 made of a less elastic material such as stainless steel, and an outer sheath 530 that surrounds the elongated body, which is made of a more elastic material such as nitinol. In one embodiment, the outer surface of the composite suture needle 500 may have the appearance of a normal, stainless steel needle.

Figure 15A:
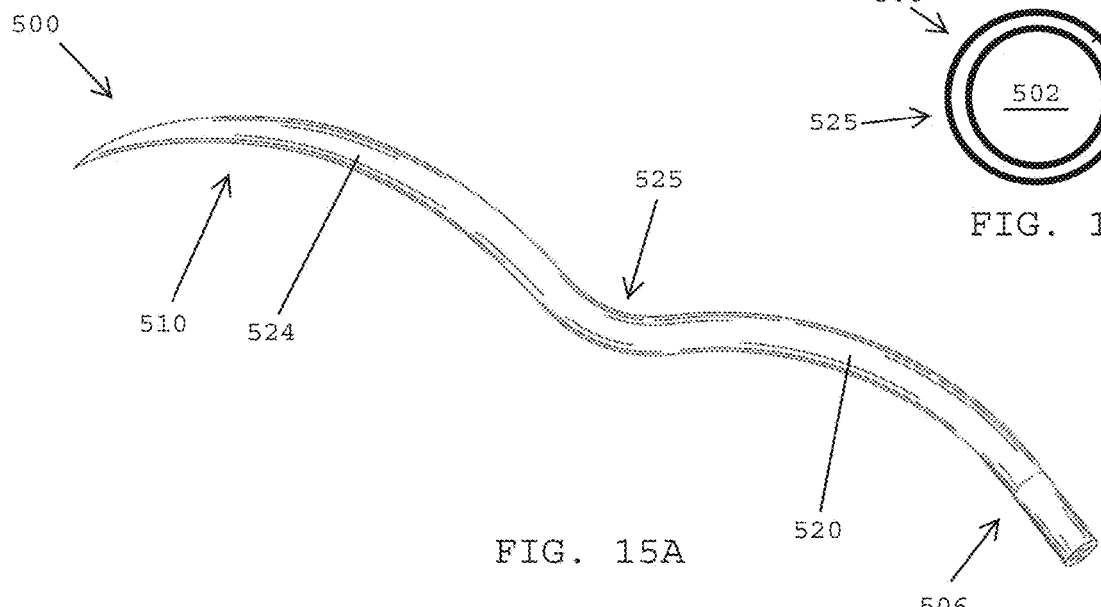
FIG. 15A is perspective view of the composite suture needle in FIG. 14A after it has been bent at the highly elastic section, in accordance with one embodiment of the present patent application.
Figure 15B:
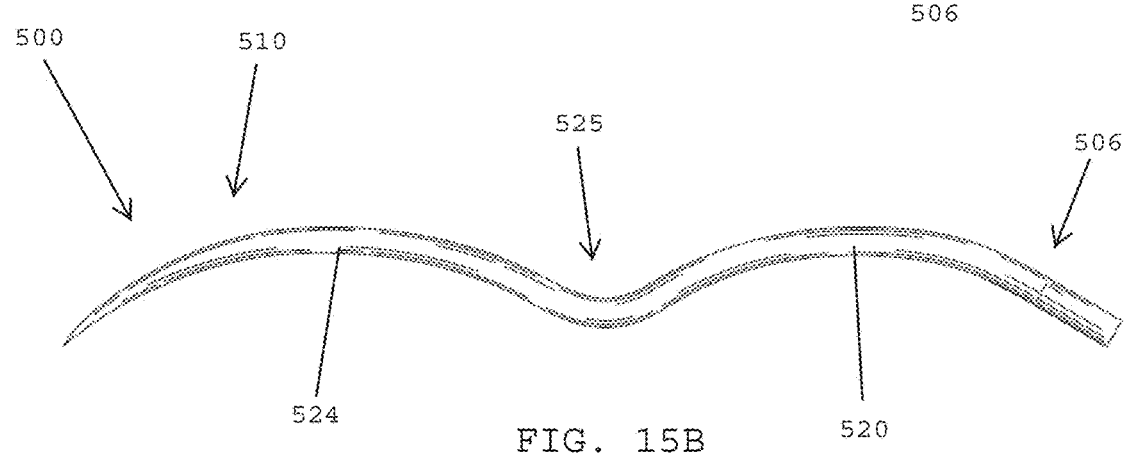
FIG. 15B is a side view of the composite suture needle shown in FIG. 15A.

In one embodiment, the needle shown and described above in FIGS. 14A and 14B may be transformed from a semi-circular or half-circle shaped configuration (FIG. 14A) to a bent configuration having a seagull shape. Referring to FIGS. 15A and 15B, in one embodiment, the composite suture needle 500 may be bent along the highly elastic region 525 to provide the needle with a seagull shaped configuration. In the seagull shaped configuration of FIGS. 15A and 15B, the suture needle 500 preferably has a smaller height or lower profile than the suture needle in the unbent configuration shown and described above in FIG. 14A. The highly elastic region 525 is preferably more bendable and less rigid than the proximal end 506 and the distal end 510 of the composite suture needle 500. As such, the proximal and distal ends 506, 510 of the composite suture needle preferably maintain their original shape in both the unbent configuration (FIG. 14A) and the bent configuration (FIGS. 15A and 15B).

Figure 16:
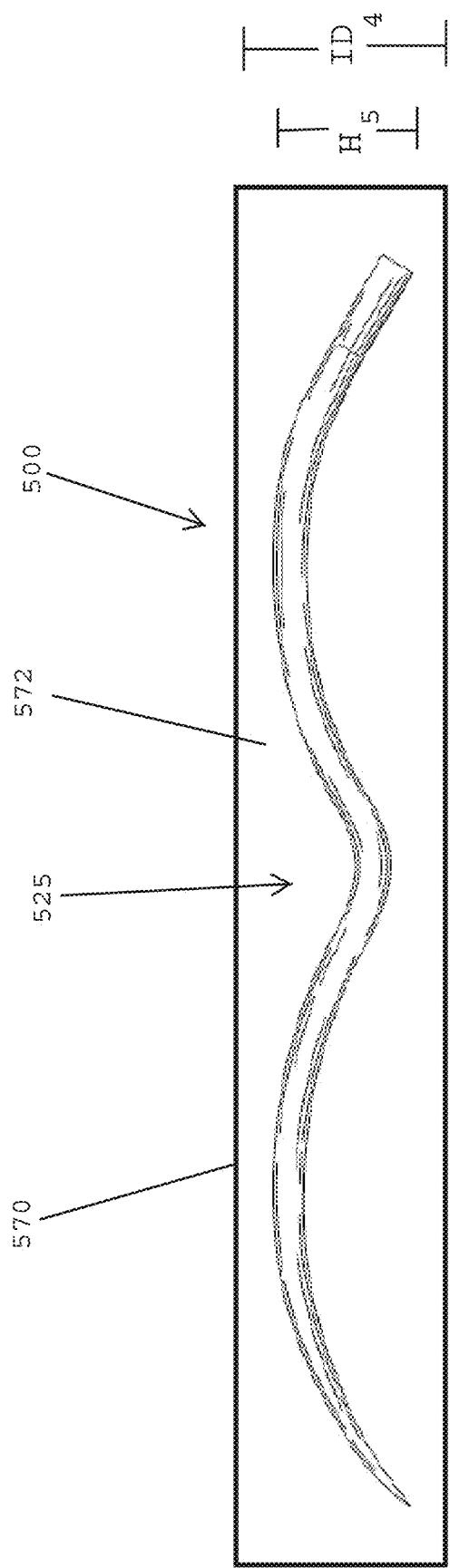
FIG. 16 shows the composite suture needle of FIGS. 15A and 15B in a bent configuration for enabling the composite suture needle to be passed through a cannula, in accordance with one embodiment of the present patent application.

Referring to FIG. 16, in one embodiment, with the highly elastic region 525 of the composite suture needle 500 being bent to place the suture needle 500 in the bent, seagull shaped configuration, the suture needle 500 may be passed through a cannula 570. In FIG. 16, the bent composite suture needle 500 having the seagull shaped configuration defines a height $H_5$ that is less than the inner diameter $ID_4$ of the lumen 572 of the cannula 570 so that the bent composite suture needle 500 may be easily passed through the length of the cannula for reaching a surgical site, without damaging the needle or creating an unsafe condition for a patient.

Referring to FIGS. 17A-17C, in one embodiment, a composite suture needle 600, having a construction that is similar to that shown and described above in FIGS. 4A-4D, 9A-9D, and/or 12A-12B, may include an elongated body 602 with a proximal end 606 and a distal end 610 having the sharpened tip 614. The composite suture needle 600 preferably includes a highly elastic region 625 having a stainless steel core and a more elastic outer sheath, which enables the elongated body 602 to be bent so that the tip 614 is adjacent the proximal end 606 of the elongated body.

In the bent configuration shown in FIGS. 17A-17C, the composite suture needle 600 may be passed through a cannula to a surgical site. Once the suture needle 600 has reached the surgical site, a surgeon may use surgical tools to transform the bent suture needle to an unbent, semi-circular configuration as shown and described herein (e.g., the embodiment of FIG. 14A). Once a suturing operation has been completed at the surgical site, a surgeon may once again bend the composite suture needle 600 at the highly elastic region 625 for reducing the dimension of the needle to remove the suture needle from the surgical site via a cannula.

In one embodiment, the elongated body of the elastic suture needle may have a bendable region provided thereon, which facilitates changing the shape and/or configuration of the suture needle to fit through a cannula (e.g., a 5 mm cannula), as disclosed in commonly assigned U.S. patent application Ser. No. 16/282,604, filed on Feb. 22, 2019, and U.S. patent application Ser. No. 16/282,652, filed on Feb. 22, 2019, the disclosures of which are hereby incorporated by reference herein.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A composite suture needle comprising:
an elongated body extending from a proximal end to a distal end, said elongated body including a distal portion with a pointed tip at a distal end thereof and a reduced diameter section having a first outer diameter, said distal portion of said elongated body including a shoulder at a proximal end thereof, the shoulder having a second outer diameter that is greater than the first outer diameter of said reduced diameter section, and wherein an entirety of said elongated body has a partially circular shape; and
a sheath overlying said reduced diameter section of said elongated body, wherein said sheath comprises a material that is more elastic than a material of said elongated body, wherein said sheath extends along said elongated body, proximally of said distal portion, so that a distal end of said sheath abuts against said shoulder of said distal portion of said elongated body, and wherein said pointed tip extends distally beyond the distal end of said sheath.

2. The composite suture needle as claimed in claim 1, wherein said sheath comprises a highly elastic material and said elongated body comprises stainless steel.

3. The composite suture needle as claimed in claim 2, wherein said highly elastic material comprises nitinol.

4. The composite suture needle as claimed in claim 2, wherein said stainless steel is selected from a group of stainless steels consisting of austenitic stainless steels, martensitic-aged (mar-aged) stainless steels, and martensitic-aged alloys.

5. The composite suture needle as claimed in claim 1, wherein said distal portion of said elongated body includes a tapered section having a proximal end including said shoulder having the second outer diameter and said tapered section has a distal end that includes said pointed tip.

6. The composite suture needle as claimed in claim 5, wherein said sheath has a proximal end, the distal end, and a lumen that extends from the proximal end to the distal end of said sheath, wherein said reduced diameter section of said elongated body is disposed within said lumen of said sheath, and wherein said lumen of said sheath has an inner diameter that is greater than or equal to the first outer diameter of said reduced diameter section of said elongated body.

7. The composite suture needle as claimed in claim 6, wherein said sheath has an outer surface that defines a third outer diameter that approximates the second outer diameter of said shoulder at the proximal end of said tapered section of said elongated body to provide a smooth transition between said tapered section and the distal end of said sheath.

8. The composite suture needle as claimed in claim 1, further comprising a suture receiving hole formed in a proximal end of a proximal portion of said elongated body.

9. A composite suture needle comprising:
an elongated body having a curved proximal body section, a curved distal body section, and a curved midsection that extends between said curved proximal body section and said curved distal body section, wherein an entirety of said elongated body has a partially circular shape, and wherein said curved midsection defines a reduced diameter section of said elongated body having a first outer diameter;

said curved proximal body section of said elongated body including a proximal shoulder located at a distal end of said curved proximal body section that defines a second outer diameter that is greater than the first outer diameter of said curved midsection of said elongated body;

said curved distal body section of said elongated body including a distal shoulder located at a proximal end of said curved distal body section that defines a second outer diameter that is greater than the first outer diameter of said curved midsection of said elongated body; and a sheath having a continuous tubular wall around the entire circumference of the sheath, the sheath is overlying said curved midsection that defines the reduced diameter section of said elongated body, wherein said sheath has a proximal end that abuts against said proximal shoulder of said curved proximal body section and a distal end that abuts against said distal shoulder of said curved distal body section, and wherein said curved midsection of said elongated body comprises a first material and said sheath comprises a second material that is more elastic than the first material of said curved midsection.

10. The composite suture needle as claimed in claim 9, wherein said curved midsection and said sheath overlying said curved midsection define a flexible region of said composite suture needle that is more elastic than said curved proximal body section and said curved distal body section of said elongated body of said composite suture needle.

11. The composite suture needle as claimed in claim 9, wherein said curved midsection of said elongated body comprises stainless steel and said sheath that overlies said curved midsection comprises nitinol.

12. The composite suture needle as claimed in claim 9, wherein said sheath has the proximal end, the distal end, and a lumen that extends from the proximal end to the distal end of said sheath, and wherein said curved midsection of said elongated body is disposed within said lumen of said sheath.

13. The composite suture needle as claimed in claim 12, wherein said curved midsection of said elongated body has the first outer diameter and said lumen of said sheath has a first inner diameter that is greater than or equal to the first outer diameter of said curved midsection of said elongated body, such that the first inner diameter of said sheath snuggly fits over the first outer diameter of said curved midsection.

14. The composite suture needle as claimed in claim 13, wherein said sheath has an outer surface defining a third outer diameter that approximates the second outer diameter of said proximal shoulder and the second outer diameter of said distal shoulder.

15. The composite suture needle as claimed in claim 9, wherein said curved proximal body section of said elongated body comprises a proximal end face and a suture receiving hole formed in the proximal end face, and wherein said curved distal body section of said elongated body comprises a tissue piercing point at a distal end thereof.

16. The composite suture needle as claimed in claim 9, wherein said sheath is attached via a thermal shrink fit process, glued or welded to said curved midsection of said elongated body.

17. The composite suture needle as claimed in claim 9, wherein said sheath overlying said curved midsection that defines the reduced diameter section of said elongated body has a partially circular shape.

18. The composite suture needle as claimed in claim 17, further comprising a suture receiving hole formed in a proximal end of said curved proximal body section.

19. The composite suture needle as claimed in claim 9, wherein connections between said sheath and said distal and proximal shoulders are configured to permit said sheath to bend with said curved midsection without sliding along said elongated body.

20. A composite suture needle comprising:

a curved proximal body section including a proximal shoulder on a distal end thereof;

a curved distal body section including a distal shoulder on a proximal end thereof and a pointed tip at a distal end thereof;

a reduced diameter section extending between said curved proximal body section and said curved distal body section, said reduced diameter section having a first outer diameter; and a continuous sheath overlying said reduced diameter section, a proximal end of said sheath abutting the proximal shoulder of said curved proximal body section and a distal end of said sheath abutting the distal shoulder of said curved distal body section, wherein the distal end of said sheath is proximal of a proximal end of the distal shoulder, wherein a second outer diameter of each of the distal and proximal shoulders approximates a third outer diameter of said sheath, and wherein an inner diameter of a lumen of said sheath is slightly larger than the first outer diameter of said reduced diameter section, such that the inner diameter of the lumen of said sheath snuggly fits over the first outer diameter of said reduced diameter section.

* * * * *